US009302100B2

(12) United States Patent  (10) Patent No.: US 9,302,100 B2
Gunderson  (45) Date of Patent: Apr. 5, 2016

(54) LEAD MONITORING FREQUENCY BASED ON LEAD AND PATIENT CHARACTERISTICS

(71) Applicant: Medtronic, Inc., Minneapolis, MN (US)

(72) Inventor: Bruce D Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/180,182

(22) Filed: Feb. 13, 2014

(65) Prior Publication Data

US 2015/0224302 A1  Aug. 13, 2015

(51) Int. Cl.
*A61N 1/00* (2006.01)
*A61N 1/08* (2006.01)
*A61N 1/37* (2006.01)
*A61N 1/05* (2006.01)

(52) U.S. Cl.
CPC *A61N 1/08* (2013.01); *A61N 1/056* (2013.01); *A61N 1/3706* (2013.01); *A61N 2001/083* (2013.01)

(58) Field of Classification Search
CPC ............... A61B 1/37; A61B 1/36; A61B 1/39
USPC .......................................................... 607/28
See application file for complete search history.

(56) References Cited

U.S. PATENT DOCUMENTS 3,602,215 A  8/1971  Parnell
4,140,131 A  2/1979  Dutcher et al.
4,825,869 A  5/1989  Sasmor et al.
5,156,149 A  10/1992  Hudrlik
5,184,614 A  2/1993  Collins et al.
5,201,808 A  4/1993  Steinhaus et al.
5,201,865 A  4/1993  Kuehn
5,224,475 A  7/1993  Berg et al.

(Continued)

FOREIGN PATENT DOCUMENTS

WO  2006119136 A1  11/2006
WO  2013181409 A1  12/2013

OTHER PUBLICATIONS (PCT/US2015/015732) PCT Notification of Transmittal of the International Search Report and the Written Opinion of the International Searching Authority.

(Continued)

*Primary Examiner* — Robert N Wieland
(74) *Attorney, Agent, or Firm* — Michael J. Ostrom

(57) ABSTRACT

A method and device for updating a frequency of determining whether a lead condition is occurring in a medical device that includes sensing a cardiac signal, determining whether a lead condition is occurring in response to the sensed cardiac signal, determining whether a first patient characteristic is satisfied during a plurality of predetermined update periods, performing a first update of a virtual lead days value associated with a number of days since implant of the lead in response to the first patient characteristic being satisfied, determining whether a patient characteristic update is satisfied in response to a second patient characteristic, different than the first patient characteristic, being satisfied, performing a second update of the virtual lead days value in response to the patient characteristic update being satisfied, and updating a frequency of determining whether the lead condition is occurring in response to the updated virtual lead days value.

23 Claims, 10 Drawing Sheets

(56) References Cited

U.S. PATENT DOCUMENTS

| | | |
|---|---|---|
| 5,344,430 A | 9/1994 | Berg |
| 5,350,410 A | 9/1994 | Kleks et al. |
| 5,354,316 A | 10/1994 | Keimel |
| 5,431,692 A | 7/1995 | Hansen et al. |
| 5,453,468 A | 9/1995 | Mascia et al. |
| 5,507,786 A | 4/1996 | Morgan et al. |
| 5,534,018 A | 7/1996 | Wahlstrand et al. |
| 5,545,186 A | 8/1996 | Olson |
| 5,549,646 A | 8/1996 | Katz |
| 5,593,431 A | 1/1997 | Sheldon |
| 5,660,183 A | 8/1997 | Chiang et al. |
| 5,713,932 A | 2/1998 | Gillberg et al. |
| 5,722,997 A | 3/1998 | Nedlungadi et al. |
| 5,741,311 A | 4/1998 | McVenes et al. |
| 5,755,742 A | 5/1998 | Schuelke |
| 5,776,168 A | 7/1998 | Gunderson |
| 5,814,088 A | 9/1998 | Paul |
| 5,861,012 A | 1/1999 | Stroebel |
| 5,891,179 A | 4/1999 | Er et al. |
| 5,897,577 A | 4/1999 | Cinbis et al. |
| 5,910,156 A | 6/1999 | Cinbis et al. |
| 5,957,861 A | 9/1999 | Combs et al. |
| 5,959,861 A | 9/1999 | Kaneko |
| 6,016,447 A | 1/2000 | Juran et al. |
| 6,129,746 A * | 10/2000 | Levine et al. ............ 607/27 |
| 6,141,585 A | 10/2000 | Prutchi et al. |
| 6,317,633 B1 | 11/2001 | Jorgenson et al. |
| 6,393,316 B1 | 5/2002 | Gillberg |
| 6,721,600 B2 | 4/2004 | Jorgenson et al. |
| 7,047,083 B2 | 5/2006 | Gunderson |
| 7,120,493 B2 | 10/2006 | Propp |
| 7,242,978 B2 | 7/2007 | Cao |
| 7,266,409 B2 | 9/2007 | Gunderson |
| 7,277,757 B2 | 10/2007 | Casavant |
| 7,289,851 B2 | 10/2007 | Gunderson |
| 7,454,249 B1 | 11/2008 | Bornzin et al. |
| 7,515,961 B2 | 4/2009 | Germanson |
| 7,574,259 B1 | 8/2009 | Pei et al. |
| 7,747,320 B1 | 6/2010 | Kroll |
| 7,783,354 B2 | 8/2010 | Gunderson |
| 7,797,047 B2 | 9/2010 | Jorgenson et al. |
| 7,974,690 B2 | 7/2011 | Kracker |
| 8,099,166 B2 | 1/2012 | Schuller |
| 8,200,330 B2 | 6/2012 | Kroll |
| 8,352,033 B2 | 1/2013 | Kroll |
| 8,355,783 B2 | 1/2013 | Goetz et al. |
| 8,401,629 B2 | 3/2013 | Stadler et al. |
| 8,463,382 B2 | 6/2013 | Jorgenson et al. |
| 8,626,293 B2 | 1/2014 | Bornzin et al. |
| 8,676,317 B1 | 3/2014 | Kroll et al. |
| 8,738,111 B2 | 5/2014 | Sweeney et al. |
| 8,812,103 B2 | 8/2014 | Kroll et al. |
| 9,008,773 B2 | 4/2015 | Gunderson |
| 2002/0120307 A1 | 8/2002 | Jorgenson |
| 2004/0064161 A1 | 4/2004 | Gunderson et al. |
| 2005/0137636 A1 | 6/2005 | Gunderson et al. |
| 2006/0116733 A1 | 6/2006 | Gunderson |
| 2006/0235476 A1 | 10/2006 | Gunderson |
| 2006/0247706 A1 | 11/2006 | Germanson et al. |
| 2006/0264777 A1 | 11/2006 | Drew |
| 2007/0100407 A1 | 5/2007 | Armstrong |
| 2007/0293903 A1 | 12/2007 | Bohn et al. |
| 2008/0161870 A1 | 7/2008 | Gunderson |
| 2008/0161872 A1 | 7/2008 | Gunderson |
| 2008/0215110 A1 | 9/2008 | Gunderson |
| 2009/0099615 A1 | 4/2009 | Kroll |
| 2009/0112292 A1 | 4/2009 | Armstrong |
| 2009/0125079 A1 | 5/2009 | Armstrong et al. |
| 2009/0270938 A1 | 10/2009 | Pei |
| 2009/0299422 A1 | 12/2009 | Ousdigian et al. |
| 2010/0023084 A1 | 1/2010 | Gunderson |
| 2010/0114222 A1 | 5/2010 | Gunderson et al. |
| 2010/0228307 A1 | 9/2010 | Kroll et al. |
| 2010/0318149 A1 | 12/2010 | Kuhn et al. |
| 2011/0009918 A1 | 1/2011 | Bornzin |
| 2011/0054558 A1 | 3/2011 | Gunderson |
| 2011/0172562 A1 | 7/2011 | Sahasrabudhe et al. |
| 2011/0184481 A1 | 7/2011 | Hoeppner et al. |
| 2011/0319957 A1 | 12/2011 | Naware et al. |
| 2012/0109235 A1 | 5/2012 | Sheldon |
| 2012/0143278 A1 | 6/2012 | Ryu |
| 2012/0158089 A1 | 6/2012 | Bocek |
| 2012/0179056 A1 | 7/2012 | Moulder et al. |
| 2012/0191153 A1 | 7/2012 | Swerdlow et al. |
| 2013/0013038 A1 | 1/2013 | Miller |
| 2013/0325080 A1 | 12/2013 | Kroll et al. |
| 2014/0324123 A1 | 10/2014 | Kroll et al. |
| 2015/0005862 A1 | 1/2015 | Kroll et al. |

OTHER PUBLICATIONS

Leong, DP, et al. "Unrecognized Failure of Narrow Caliber Defibrillation Lead: The Role of Defibrillation Threshold Testing in Identifying an Unprotected Individual" PACE 2012; 1-2.

(PCT/US2014/021010) PCT Notification of Transmittal of the International Search Report and the Written Opinion of the International Searching Authority.

"ICD Lead Failure Detection Through High Frequency Impedance", by Daniel T. Kollmann et al., IEEE, 2014, pp. 6487-9492.

(PCT/US2015/036544) PCT Notification of Transmittal of the International Search Report and the Written Opinion of the International Searching Authority, Mailed Sep. 3, 2015, 11 pages.

* cited by examiner

LEAD MONITORING FREQUENCY BASED ON LEAD AND PATIENT CHARACTERISTICS

RELATED APPLICATION

Cross-reference is hereby made to commonly assigned U.S. patent application Ser. No. 14/180,162, filed on even date herewith entitled "LEAD MONITORING FREQUENCY BASED ON LEAD AND PATIENT CHARACTERISTICS" and U.S. patent application Ser. No. 14/180,201, filed on even date herewith entitled "LEAD MONITORING FREQUENCY BASED ON LEAD AND PATIENT CHARACTERISTICS", and incorporated by reference in its entirety.

FIELD OF THE DISCLOSURE

The disclosure relates generally to medical devices configured for delivering electrical therapies to a patient, and in particular, the disclosure relates to a method and device for monitoring changes in lead integrity in a medical device.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical signals, e.g., stimulation, to such organs or tissues. Some medical devices may employ one or more elongated electrical leads having electrodes positioned thereon for delivering and/or receiving signals. For example, electrodes may be included for use in one or both of the delivery of therapeutic electrical signals to such organs or tissues, and the sensing of intrinsic electrical signals within the patient, which may be generated by such organs or tissue. In addition, the elongated lead may include other sensors positioned thereon for sensing physiological parameters of a patient.

Medical leads may be configured to allow the electrodes or other sensors to be positioned at desired locations for delivery of therapeutic electrical signals or sensing. For example, the electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical signals to the heart via electrodes carried by one or more implantable medical leads. The therapeutic electrical signals may include pulses or shocks for pacing, cardioversion, or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Implantable medical leads typically include a lead body containing one or more elongated electrical conductors that extend through the lead body from a connector assembly provided at a proximal lead end to one or more electrodes located at the distal lead end or elsewhere along the length of the lead body. The conductors connect signal generation and/or sensing circuitry within an associated implantable medical device housing to respective electrodes or sensors. Some electrodes may be used for both delivery of therapeutic signals and sensing. Each electrical conductor is typically electrically isolated from other electrical conductors and is encased within an outer sheath that electrically insulates the lead conductors from body tissue and fluids.

Medical lead bodies implanted for cardiac applications tend to be continuously flexed by the beating of the heart. Other stresses may be applied to the lead body, including the conductors therein, during implantation or lead repositioning. Patient movement can cause the route traversed by the lead body to be constricted or otherwise altered, causing stresses on the lead body and conductors. In rare instances, such stresses may fracture a conductor within the lead body. The fracture may be continuously present, or may intermittently manifest as the lead flexes and moves during normal day to day patient activity and/or contraction of a beating heart.

Additionally, the electrical connection between medical device connector elements and the lead connector elements can be intermittently or continuously disrupted. For example, connection mechanisms, such as set screws, may be insufficiently tightened at the time of implantation, followed by a gradual loosening of the connection. Also, lead pins may not be completely inserted.

Lead fracture, disrupted connections, or other causes of short circuits or open circuits may be referred to, in general, as lead integrity conditions. In the case of cardiac leads, sensing of an intrinsic heart rhythm through a lead can be altered by lead integrity conditions. Identifying lead integrity conditions may be challenging, particularly in a clinic, hospital or operating room setting, due to the often intermittent nature of lead integrity conditions.

When these lead problems manifest themselves, it is necessary for the clinician to diagnose the nature of the lead related condition from the available data, IMD test routines, and patient symptoms. Once diagnosed, the clinician must take corrective action, for example, re-program to unipolar polarity, open the pocket to replace the lead, reposition the electrodes or sensors, or tighten the proximal connection.

Lead impedance data and other parameter data, for example, without limitation, electrogram (EGM), battery voltage, switching from bipolar to unipolar configuration, error counts, and LOC/LOS data, may be compiled and displayed on a programmer screen and/or printed out for analysis by the clinician. The clinician may also undertake real time IMD parameter reprogramming and testing while observing the monitored surface ECG to try to pinpoint a suspected lead related condition that is indicated by the data and/or patient and/or device symptoms.

Several approaches have been suggested to provide physicians with information and/or early detection or prevention of these lead-related conditions. Commonly assigned U.S. Pat. No. 5,861,012 (Stroebel), incorporated herein by reference, describes several approaches to automatically determine the pacing threshold. Periodically, a pacing threshold test is conducted wherein the pacing pulse width and amplitude are reduced to determine chronaxie and rheobase values to capture the heart. These threshold test data are stored in memory, and used to calculate a "safety margin" to ensure capture.

Certain external programmers that address the analysis of such data and symptoms include those disclosed in the following U.S. Pat. No. 4,825,869 (Sasmor et al.); U.S. Pat. No. 5,660,183 (Chiang et al.); and U.S. Pat. No. 5,891,179 (E R et al.), all incorporated herein by reference. The '869 patent describes processing a variety of uplinked, telemetered atrial and ventricular EGM data, stored parameter and event data, and the surface ECG in rule-based algorithms for determining various IPG and lead malfunctions. The '183 patent also considers patient symptoms in an interactive probability based expert system that compares data and patient systems to stored diagnostic rules, relating symptoms to etiologies so as to develop a prognosis. The '179 patent discloses a programmer that can be operated to provide a kind of time-varying display of lead impedance values in relation to upper and lower impedance limits. The lead impedance values are derived from pacing output pulse current and voltage values. These values are then either measured and stored in the IPG memory from an earlier time or represent current, real-time values that are telemetered to the programmer for processing and display.

Prior art detection of lead-related conditions and various IPG responses to such detection are set forth in the following U.S. Pat. No. 4,140,131 (Dutcher et al.); U.S. Pat. No. 4,549,548 (Wittkampf et al.); U.S. Pat. No. 4,606,349 (Livingston et al.); U.S. Pat. No. 4,899,750 (Ekwall); U.S. Pat. No. 5,003,975 (Hafelfinger et al.); U.S. Pat. No. 5,137,021 (Wayne et al.); U.S. Pat. No. 5,156,149 (Hudrlik); U.S. Pat. No. 5,184,614 (Collins); U.S. Pat. No. 5,201,808 (Steinhaus et al.); U.S. Pat. No. 5,201,865 (Kuehn); U.S. Pat. No. 5,224,475 (Berg et al.); U.S. Pat. No. 5,344,430 (Berg et al.); U.S. Pat. No. 5,350,410 (Kieks et al.); U.S. Pat. No. 5,431,692 (Hansen et al.); U.S. Pat. No. 5,453,468 (Williams et al.); U.S. Pat. No. 5,507,786 (Morgan et al.); U.S. Pat. No. 5,534,018 (Walhstrand et al.); U.S. Pat. No. 5,549,646 (Katz et al.); U.S. Pat. No. 5,722,997 (Nedungadi et al.); U.S. Pat. No. 5,741,311 (McVenes et al.); U.S. Pat. No. 5,755,742 (Schuelke et al.); and U.S. Pat. No. 5,814,088 (Paul et al.). All of these patents are incorporated herein by reference.

Because implanted leads can be critical to providing life sustaining therapy and may fail at various rates, identification of lead integrity conditions may allow modifications of the therapy or sensing, or lead replacement. Ideal lead monitoring would include continuous monitoring of lead characteristics using related characteristics, such as impedance and electrogram signals of the lead. However, such continuous monitoring is not possible given the limited resources within the implantable medical device. While the occurrence of lead integrity issues tends to be rare, many factors may contribute to lead failure. For example, the age of the patient may be contribute to the occurrence of issues leading to failure, with an increase in the number of lead integrity issues occurring for younger patients. Other factors may include the gender of the patient, the level of activity of the patient, or how long the device has been implanted in the patient, etc. Therefore, what is needed is a method and apparatus for varying lead monitoring when needed based on multiple factors associated with increased failure risk.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
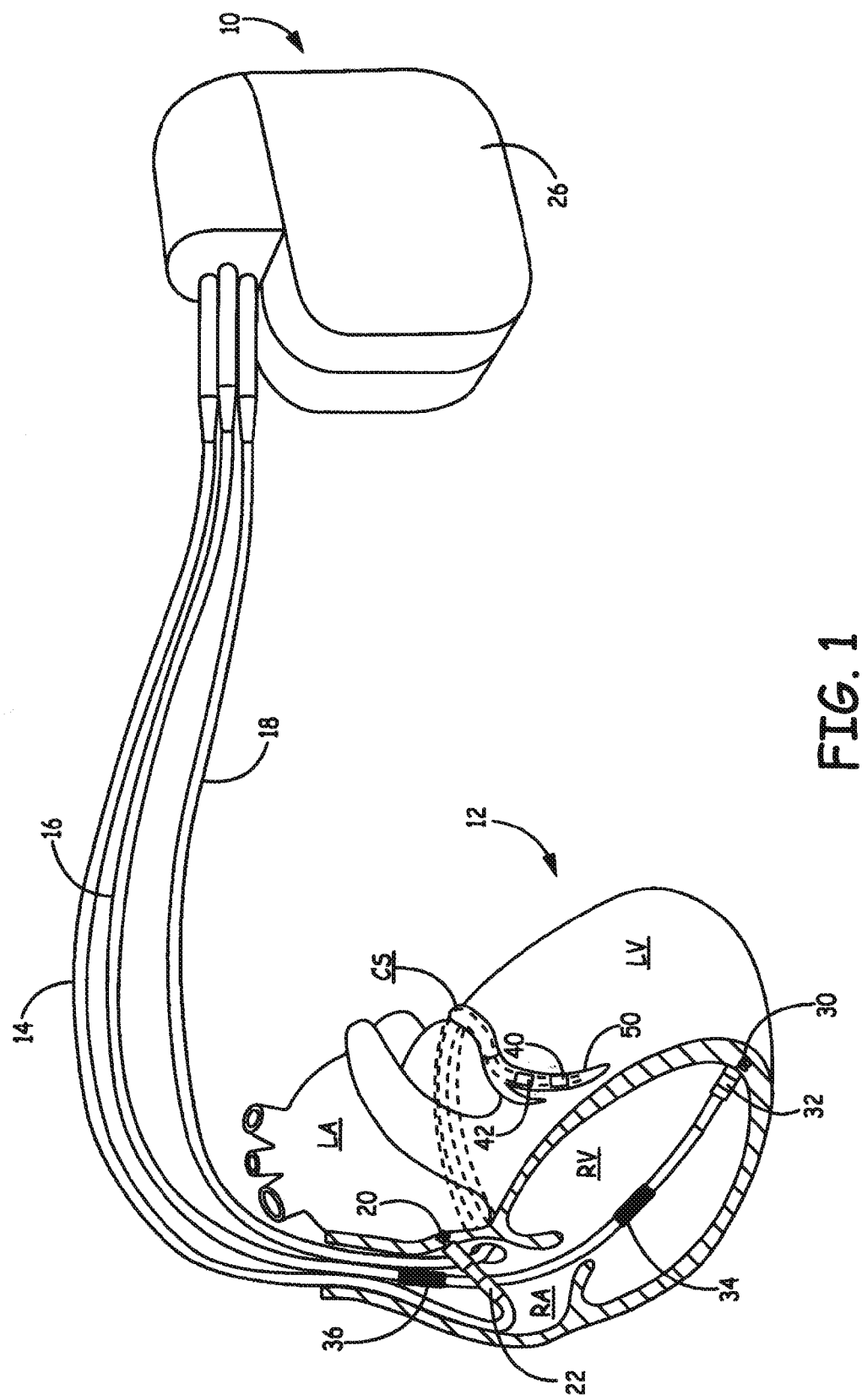
FIG. 1 is a schematic representation of an implantable medical device (IMD) capable of delivering high voltage and low voltage therapies to a heart.

FIG. 1 is a schematic representation of an implantable medical device (IMD) 10 capable of delivering high voltage and low voltage therapies to heart 12. IMD 10 is coupled to heart 12 via leads 14, 16 and 18. Right atrial lead 14 extends from IMD 10 to the right atrium (RA) and carries distal electrodes 20 and 22 for sensing cardiac electrical signals and delivering pacing pulses in the RA.

Right ventricular lead 16 carries a tip electrode 30 and a ring electrode 32 for sensing cardiac electrical signals and delivering pacing pulses in the RV. RV lead 16 additionally carries high voltage coil electrodes 34 and 36, referred to herein as the RV coil electrode 34 and the superior vena cava (SVC) coil electrode 36, for delivering high voltage cardioversion and defibrillation shocks in response to detecting a shockable tachyarrhythmia from sensed cardiac signals. In addition, a housing electrode 26, also referred to as a CAN electrode, can be formed as part of the outer surface of the housing of IMD 10 and be used as an active electrode in combination with coil electrodes 34 and/or 36 during shock delivery.

A coronary sinus (CS) lead 18 is shown extending into a cardiac vein 50 via the RA and coronary sinus for positioning electrodes 40 and 42 for sensing cardiac signals and delivering pacing pulses along the left ventricle. In some examples, CS lead 18 may additionally carry electrodes for positioning along the left atrium for sensing and stimulation along the left atrial chamber.

The depicted positions in or about the right and left heart chambers are merely illustrative. Other leads and pace/sense electrodes and/or high voltage electrodes can be used instead of, or in combination with, any one or more of the depicted leads and electrodes shown in FIG. 1. Lead and electrode configurations are not limited to transvenous leads and intravenous or intracardiac electrodes as shown in FIG. 1. In some embodiments, an IMD system may include subcutaneous electrodes, which may be carried by an extravenous lead extending from IMD 10 or leadless electrodes incorporated along the IMD housing.

IMD 10 is shown as a multi-chamber device capable of sensing and stimulation in three or all four heart chambers. It is understood that IMD 10 may be modified to operate as a single chamber device, e.g. with a lead positioned in the RV only, or a dual chamber device, e.g. with a lead positioned in the RA and a lead positioned in the RV. In general, IMD 10 may be embodied as any single, dual or multi-chamber device including lead and electrode systems for delivering at least a high voltage therapy and may be configured for delivering both high voltage shock pulses and low voltage pacing pulses.

Figure 2:
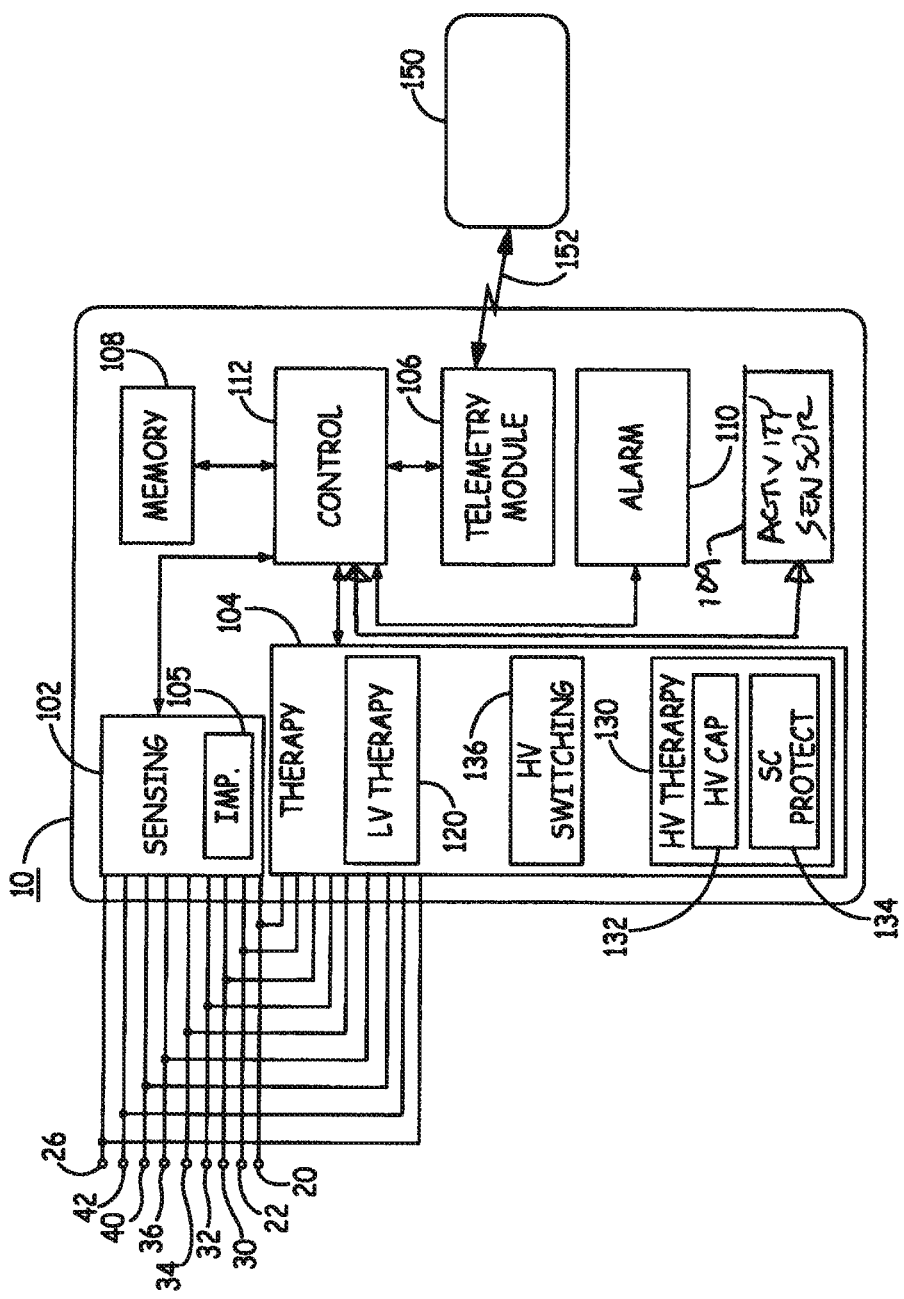
FIG. 2 is a functional block diagram of the IMD shown in FIG. 1 according to an illustrative embodiment.

FIG. 2 is a functional block diagram of the IMD 10 shown in FIG. 1 according to an illustrative embodiment. IMD 10 includes a sensing module 102, a therapy delivery module 104, a telemetry module 106, memory 108, and a control unit 112, also referred to herein as "controller" 112.

Sensing module 102 is coupled to electrodes 20, 22, 30, 32, 34, 36, 40, 42 and housing electrode 26 (all shown in FIG. 1) for sensing cardiac electrogram (EGM) signals. Sensing module 102 monitors cardiac electrical signals for sensing signals attendant to the depolarization of myocardial tissue, e.g. P-waves and R-waves, from selected ones of electrodes 20, 22, 26, 30, 32, 34, 36, 40, and 42 in order to monitor electrical activity of heart 12. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, controller 112 selects the electrodes to function as sense electrodes, or the sensing vector, via the switch module within sensing module 102.

Sensing module 102 may include multiple sensing channels, each of which may be selectively coupled to respective combinations of electrodes 20, 22, 26, 30, 32, 34, 36, 40, and 42 to detect electrical activity of a particular chamber of heart 12, e.g. an atrial sensing channel and a ventricular sensing channel. Different sensing channels may additionally or alternatively be coupled to various electrode combinations for providing both near field (NF) sensing vectors and far field (FF) sensing vectors. For example, a NF sensing vector may be sensed between RV tip electrode 30 and RV ring electrode 32. A FF sensing vector may be sensed between RV coil electrode 34 and SVC coil electrode 36. Each sensing channel may comprise an amplifier that outputs an indication to controller 112 in response to sensing of a cardiac depolarization, in the respective chamber of heart 12. In this manner, controller 112 may receive sense event signals corresponding to the occurrence of R-waves and P-waves in the various chambers of heart 12. Sensing module 102 may further include digital signal processing circuitry for providing controller 112 with digitized EGM signals, which may be used to determine EGM signal features or for signal morphology analysis in some embodiments.

Sensing module 102 and control unit 112 are configured to monitor the patient's cardiac rhythm for determining a need for therapy delivery and for timing therapy delivery. In response to detecting a tachyarrhythmia, controller 112 controls therapy delivery module 104 to deliver a therapy according to programmed therapies stored in memory 108.

Sensing module 102 may include impedance monitoring circuitry 105 for measuring current between a measurement pair of electrodes 20 through 42 in response to a drive signal. The drive signal is generally a low voltage signal, and impedance measurements may be used by control 112 to detect short circuit conditions or other lead-related issues detectable when a low voltage drive signal is used. Such low voltage impedance measurements may be performed periodically or in response to loss of pacing capture or a change in pacing threshold to detect lead-related issues. As will be described herein, impedance monitoring may be controlled and adjusted to promote the identification of a short circuit condition, as evidenced by a decrease in impedance.

Sensing module 102 provides control unit 112 digitized EGM signals for detecting a possible insulation breach and short circuit condition in some embodiments. As further described below, control unit 112 includes processing circuitry for analyzing the EGM signal to detect a signature noise waveform that is characteristic of a short circuit condition. In particular, a high priority is given to monitoring for a short circuit condition that could lead to shorting of a HV shock delivered to treat a malignant tachyarrhythmia. Real-time monitoring for a short circuit condition is described herein. It is contemplated, however, that identification of a short circuit condition may be performed during post processing. An epoch of data (e.g. 10 sec) could be stored at regular intervals in the memory 108 or triggered storage based on a detected event. The data may be post-processed either within the IMD or an external device.

Therapy delivery module 104 is coupled to electrodes 20, 22, 26, 30, 32, 34, 36, 40, and 42 for delivering electrical stimulation therapy to the patient's heart. In some embodiments, therapy delivery module 104 includes low voltage (LV) therapy circuitry 120 including a pulse generator for generating and delivering LV pacing pulses during bradycardia pacing, cardiac resynchronization therapy (CRT), and anti-tachycardia pacing (ATP). Control unit 112 controls LV therapy circuitry 120 to deliver pacing pulses according to programmed control parameters using electrodes pacing electrodes 20, 22, 30, 32, 40 and/or 42 for example. Electrodes 20, 22, 30 32, 40 and 42 are generally referred to a "low voltage" electrodes because they are normally used for delivering relatively low voltage therapies such as pacing therapies as compared to the high voltage therapies, i.e. cardioversion and defibrillation therapies, delivered by high voltage coil electrodes 32 and 34. However, as will be described herein, in some instances LV electrodes 20, 22, 30, 32 40 and 42 may be used for delivering a high voltage therapy in response to detection of a high voltage short circuit condition.

Therapy delivery module 104 includes high voltage (HV) therapy delivery circuitry 130 for generating and delivering high voltage cardioversion and defibrillation shock pulses. HV therapy delivery circuitry 130 includes HV capacitors 132 that are charged in response to detecting a shockable cardiac rhythm, e.g. a ventricular tachycardia or ventricular fibrillation. After determining HV capacitors 132 have reached a targeted charge voltage, according to a programmed shock energy, HV therapy delivery 130 delivers a shock pulse via selected HV electrodes, e.g. coil electrodes 34, 36 and housing electrode 26.

HV therapy circuitry 130 includes short circuit (SC) protection circuitry for protecting IMD 10 against a short circuit fault during HV therapy delivery. In one embodiment, SC protection circuitry 134 monitors the current during the shock pulse delivery and in response to a relatively high current, i.e.

very low impedance, SC protection circuitry 134 immediately terminates the shock pulse, e.g. by an electronic switch, to prevent damage to the circuitry of IMD 10. The HV short circuit condition would prevent delivery of the HV shock to the heart and would fail to terminate a detected shockable rhythm. By protecting the IMD circuitry from the SC fault, controller 112 remains operable to alter the HV therapy delivery to still treat the tachyarrhythmia and/or control therapy delivery module 104 to deliver alternative electrical stimulation therapies.

In response to identifying a short circuit condition, controller 112 may store in memory 108 an electrode vector and polarity combination being used that provided evidence of a short circuit condition. This information may be retrieved and used by a clinician in resolving the short circuit condition, e.g. by replacing a lead or reprogramming the therapy delivery electrode configuration and polarity. This information may be used by controller 112 in selecting electrode vectors and polarities for delivering future HV and/or LV therapies.

Therapy delivery module 104 includes HV switching circuitry 136 used for controlling the pathway through which HV capacitors 132 are discharged. HV switching circuitry 136 may include a switch array, switch matrix, multiplexer, or any other type of switching device suitable to selectively couple combinations of low voltage electrodes (e.g. electrodes 20, 22, 30, 32, 40 and 42) and/or high voltage electrodes (e.g. electrodes 34 and 36) and housing electrode 26 to HV therapy circuitry 130. In some examples, controller 112 selects a shock vector using any of HV coil electrodes 34, 36 and housing electrode 26. As will be described below, controller 112 may select the polarity of the electrodes included in the shock vector using switching circuitry 136.

In some embodiments, the HV capacitors may be coupled to multiple pacing electrode cathodes simultaneously, e.g. any combination or all of LV electrodes 20, 22, 30, 32, 40 and 42 for delivering a HV shock in response to a HV short circuit condition. The anode may be any of the coil electrodes 34, 36, housing electrode 26 or combination of remaining LV electrodes 20, 22, 30, 32, 40 and 42 or any other housing based or lead based electrodes that may be available in the particular IMD system. Pacing capacitors coupled to electrodes 20, 22, 30, 32, 40 and 42 included in LV therapy circuitry 120 may be used in distributing the HV charge remaining on the HV capacitor(s) 132 in some embodiments in an attempt to deliver a needed shock therapy. In this case the pacing capacitors are rated for adequately high voltage to distribute the shock energy among selected electrodes.

Controller 112 may be embodied as a processor including any one or more of a microprocessor, a digital signal processor (DSP), an application specific integrated circuit (ASIC), a field-programmable gate array (FPGA), or equivalent discrete or integrated logic circuitry. In some examples, controller 112 may include multiple components, such as any combination of one or more microprocessors, one or more controllers, one or more DSPs, one or more ASICs, or one or more FPGAs, as well as other discrete or integrated logic circuitry. The functions attributed to controller 112 herein may be embodied as software, firmware, hardware or any combination thereof. Controller 112 includes a therapy control unit that controls therapy module 104 to deliver therapies to heart 12 according to a selected one or more therapy programs, which may be stored in memory 108. Controller 112 and associated memory 108 are coupled to the various components of IMD 10 via a data/address bus.

Memory 108 stores intervals, counters, or other data used by controller 112 to control sensing module 102, therapy delivery module 104 and telemetry module 106. Such data may include intervals and counters used by controller 112 for detecting a heart rhythm and to control the delivery of therapeutic pulses to heart 12. Memory 108 also stores intervals for controlling cardiac sensing functions such as blanking intervals and refractory sensing intervals. Events (P-waves and R-waves) sensed by sensing module 102 may be identified based on their occurrence outside a blanking interval and inside or outside of a refractory sensing interval.

Memory 108 may store computer-readable instructions that, when executed by controller 112, cause IMD 10 to perform various functions attributed throughout this disclosure to IMD 10. The computer-readable instructions may be encoded within memory 108. Memory 108 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Tachyarrhythmia detection algorithms may be stored in memory 108 and executed by controller 112 for detecting ventricular tachycardia (VT), ventricular fibrillation (VF) as well as discriminating such ventricular tachyarrhythmias, generally referred to herein as "shockable rhythms" from atrial or supraventricular tacharrhythmias, such as sinus tachycardia and atrial fibrillation (A FIB). Ventricular event intervals (R-R intervals) sensed from the EGM signals are commonly used for detecting cardiac rhythms. Additional information obtained such as R-wave morphology, slew rate, other event intervals (e.g., P-P intervals and P-R intervals) or other sensor signal information may be used in detecting, confirming or discriminating an arrhythmia. Reference is made to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals, all of which patents are incorporated herein by reference in their entirety. The techniques described herein for detecting a short circuit condition and responding thereto may be implemented in the types of devices disclosed in the above-referenced patents.

In response to detecting a shockable rhythm, a programmed therapy is delivered by therapy delivery module 104 under the control of controller 112. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 108. For example, on initial detection of a ventricular tachycardia, an anti-tachycardia pacing therapy may be selected and delivered. On redetection of the ventricular tachycardia, a more aggressive anti-tachycardia pacing therapy may be scheduled. If repeated attempts at anti-tachycardia pacing therapies fail, a HV cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that ventricular fibrillation is identified, high frequency burst stimulation may be employed as the initial attempted therapy. Subsequent therapies may be delivery of HV defibrillation shock pulses, typically in excess of 5 Joules, and more typically in the range of 20 to 35 Joules. Lower energy levels may be employed for cardioversion. In the absence of a HV short circuit condition, the defibrillation pulse energy may be increased in response to failure of an initial pulse or pulses to terminate fibrillation.

IMD 10 may additionally be coupled to one or more physiological sensors. Physiological sensors may include pressure sensors, accelerometers, flow sensors, blood chemistry sensors, activity sensors or other physiological sensors known for use with implantable cardiac stimulation devices. Physiological sensors may be carried by leads extending from IMD 10 or incorporated in or on the IMD housing. Sensor signals may be used in conjunction with EGM signals for detecting and/or confirming a heart rhythm. An activity sensor 109 may be optionally included in some examples of IMD 10. Activity sensor 109 may include one or more accelerometers. Activity sensor 109 may additionally or alternatively include other sensors such as a heart sounds sensor, a pressure sensor, or an oxygen saturation sensor. Activity sensor 109 may detect respiration via one or more electrodes. Information obtained from activity sensor 109 may be used to determine activity level, posture, blood oxygen level or respiratory rate, for example, leading up to, or at the time of the abnormal heart rhythm. In some examples, this information from activity sensor 109 may be used by IMD 10 to aid in the determination as to whether to update the lead integrity monitoring frequency, as described below in detail.

Telemetry module 106 is used for transmitting data accumulated by IMD 10 wirelessly to an external device 150, such as a programmer, home monitor, or handheld appliance. Examples of communication techniques used by IMD 10 include low frequency or radiofrequency (RF) telemetry, which may be an RF link established via Bluetooth, WiFi, or MICS. IMD 10 may receive programming commands and algorithms from external device 150 via telemetry link 152 with telemetry module 106. For example, external device 150 may be used to program SC detection parameters used by controller 112. Telemetry module 106 may be controlled by controller 112 for delivering a patient or clinician alert or notification to external device 150 in response to detecting a short circuit condition.

IMD 10 may optionally be equipped with alarm circuitry 110 for notifying the patient or other responder that a patient alert condition has been detected by IMD 10. In one embodiment, the alarm 110 may emit an audible tone or notification to alert the patient or a responder that immediate medical attention is required. For example, when a short circuit condition is detected, particularly a short circuit involving HV coil electrodes 34 and 36, alarm 110 may be used to notify the patient, a caregiver or other responder that medical attention is required. In some embodiments, alarm 110 calls an emergency number directly via a wireless communication network.

Figure 3:
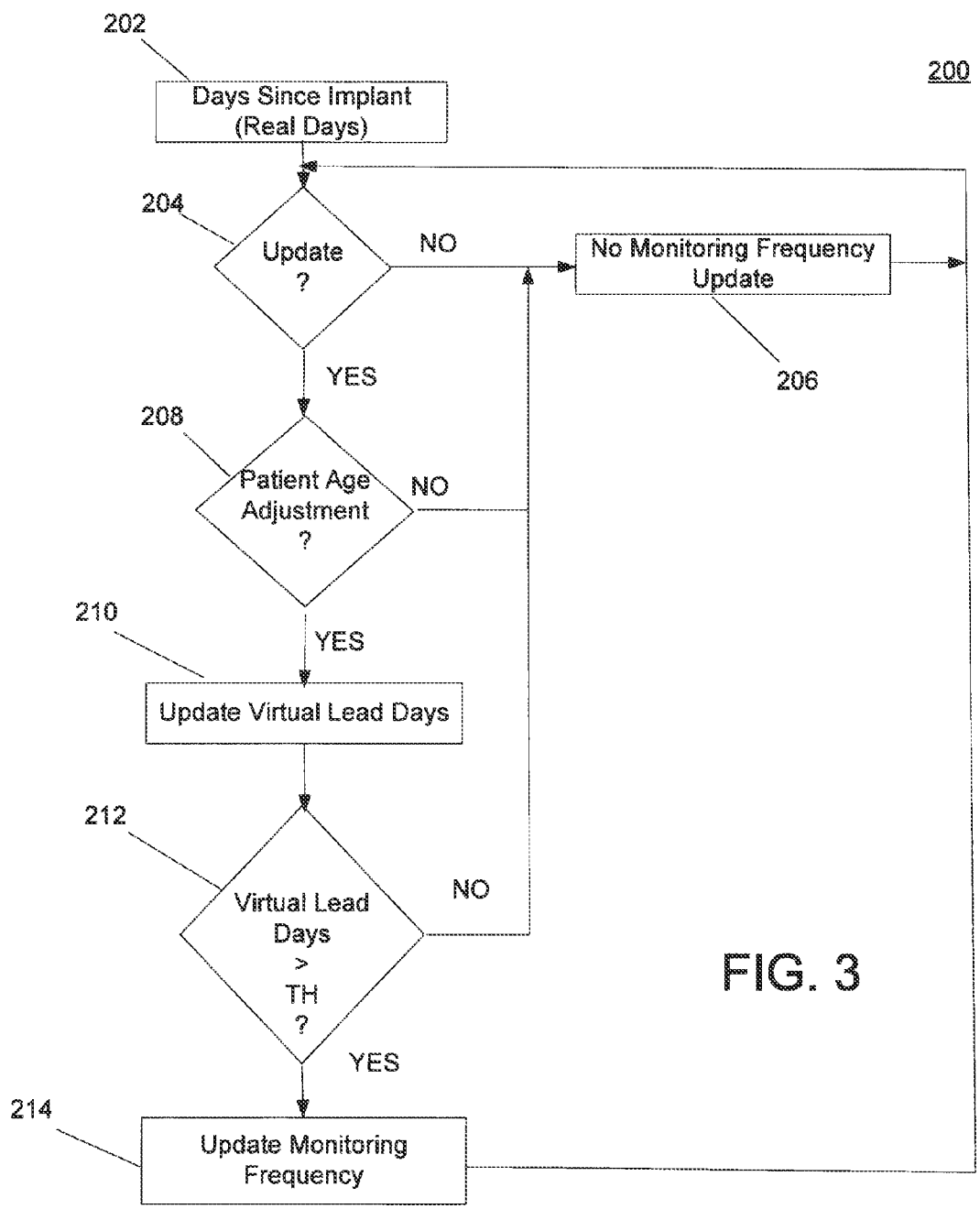
FIG. 3 is a flowchart of an exemplary method of determining lead integrity monitoring frequency in a medical device according to an embodiment of the disclosure.

FIG. 3 is a flowchart of an exemplary method of determining lead integrity monitoring frequency in a medical device according to an embodiment of the disclosure. During implant of the device, information such as one or more of the age of the patient, the gender of the patient, and the date of implant are stored in the device by being input by the implanting physician using a programmer. In addition, the initial frequency at which lead integrity monitoring, such as impedance monitoring, for example, may also be set by the physician via the programmer, or a default starting frequency may be utilized. According to one embodiment, the device may be initially programmed, either by default or by the physician, so that lead integrity monitoring using impedance measurements is performed four times per day, and may be increased once one or more of these patient characteristics are satisfied, as described in detail below. Once a predetermined period of time or a predetermined event occurs subsequent to the implant, updating of the frequency of the lead integrity monitoring according to the present disclosure is determined. For example, according to an embodiment, lead integrity issues may be monitored using impedance measurements taken four times per day, and the device performs the determination 200 of whether to update the lead integrity monitoring frequency once per day, i.e. once every 24 hours. However, the frequency of the lead impedance monitoring and/or the frequency at which the determination of whether to update the lead integrity monitoring frequency 200 may also initially be performed at other desired frequencies, such as twice a day or once every two days, for example.

As illustrated in FIG. 3, according to an embodiment of the present disclosure, the device monitors lead integrity using lead impedance measurements taken four times per day, and initially makes the determination as to whether to update the lead integrity monitoring frequency 200 by determining whether the predetermined period of time, i.e., 24 hours, has expired since implant of the device, Block 204. If the update time period has not expired, NO in Block 204, no monitoring frequency update is performed, Block 206. Once the initial update time has expired, YES in Block 204, the device determines the current age of the patient, compares the patient's current age to a predetermined patient age adjustment threshold, and determines whether to update the frequency at which the lead integrity monitoring is performed based on the determined age of the patient, Block 208.

For example, in order to determine whether a patient age adjustment is to occur, Block 208, the device determines whether the age of the patient is within a predetermined patient age range. According to one embodiment, the patient age range is less than twenty years. Other patient age ranges may be utilized, such as whether the age of the patient is greater than 20 years but less than 40 years. If the current patient age is not within the patient range, NO in Block 208, no update of the frequency of performance of the lead integrity monitoring is made, Block 206, the device continues performing the lead integrity monitoring at the current monitoring frequency, and waits until the next frequency update monitoring is scheduled to occur, Block 204, i.e., the device again waits for 24 hours, and the process is repeated.

If the patient is determined to be within the predetermined patient age range, YES in Block 208, a patient age adjustment is determined to be needed. According to one embodiment, the device stores a value associated with the virtual lead days since implant of the device, which is initially equal to the running actual or "real days" since implant of the device, Block 202. If the patient age adjustment is determined to be needed, YES in Block 208, the device updates the number of virtual lead days since implant of the lead, Block 210, by increasing the number of virtual lead days, Block 202, by a predetermined number of days associated with a patient age adjustment. Therefore, the value of the virtual days becomes the sum of the running real days since implant of the device and the predetermined number of days associated with the patient age adjustment.

The device may update the stored virtual lead days, Block 210, by increasing the virtual lead days by a predetermined amount when the patient is determined to be within the patient adjustment range, Block 208. In one embodiment the device increases the virtual lead days, Block 210, by adding four days, to the currently stored virtual lead days, for example. In this way, for each day the patient is determined to be in the predetermined patient age range, YES in Block 208, the stored virtual lead days is updated in Block 210 by being increased by four days.

Once the virtual lead days have been updated in Block 210, the device compares the updated virtual lead days to a virtual lead days threshold to determine whether the value of updated virtual lead days is greater than the virtual lead days threshold, Block 212. If the updated virtual lead days is not greater than the virtual lead days threshold, NO in Block 212, no monitoring frequency update is performed, Block 206, and the process is repeated once the next predetermined period of time, i.e., 24 hours has expired, YES in Block 204. If the current updated virtual lead days is determined to be greater than the virtual lead days threshold, YES in Block 212, the frequency of the lead integrity monitoring is updated by a patient age adjustment value, Block 214, and the process is repeated once the next predetermined period of time, i.e., 24 hours has expired, YES in Block 204.

According to one embodiment of the disclosure, the virtual lead days threshold may be set as five years so that the frequency of the lead integrity monitoring is increased in Block 214 once the stored updated virtual lead days is determined to be greater than five years, Block 212. The frequency of the lead integrity monitoring may be updated by increasing the number of daily impedance measurements used to evaluate lead integrity. In one embodiment, the device increases the number of daily impedance values utilized to determine lead integrity issues from the initial four impedance values per day to eight values per day.

Figure 4:
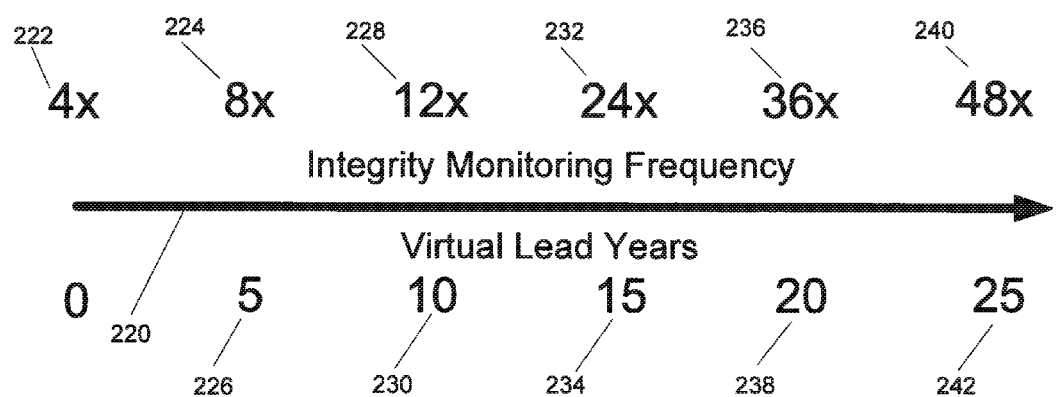
FIG. 4 is a timeline illustrating updating of the frequency of lead integrity monitoring according to an embodiment of the present disclosure.

As illustrated in FIG. 3, the determination of whether to update the lead integrity monitoring frequency 200 of the present invention occurs once every 24 hours, and includes updating the stored virtual lead days if the patient is determined to be within the patient age range, Block 208, and updating the lead monitoring frequency if the stored updated virtual lead days is greater than the virtual lead days threshold, Block 212. FIG. 4 is a timeline illustrating updating of the frequency of lead integrity monitoring according to an embodiment of the present disclosure. As illustrated in FIG. 4, in order to update the frequency of lead integrity monitoring, the device increases the number of daily impedance values utilized to determine lead integrity issues, indicated on the upper portion of timeline 220, from the initial four impedance values determined per day 222 to eight impedance values determined per day 224 once the accumulated virtual days, indicated on the lower portion of timeline 220, are greater than 5 years 226. The device then subsequently increases the number of daily impedance values utilized to determine lead integrity issues to twelve impedance values determined per day 228 once the accumulated virtual days are greater than ten years 230, to twenty-four impedance values determined per day 232 once the accumulated virtual days are greater than fifteen years 234, to thirty-six impedance values determined per day 236 once the accumulated virtual days are greater than twenty years 238, and to forty-eight impedance values determined per day 240 once the accumulated virtual days are greater than twenty-five years 242, and so forth.

Figure 5:
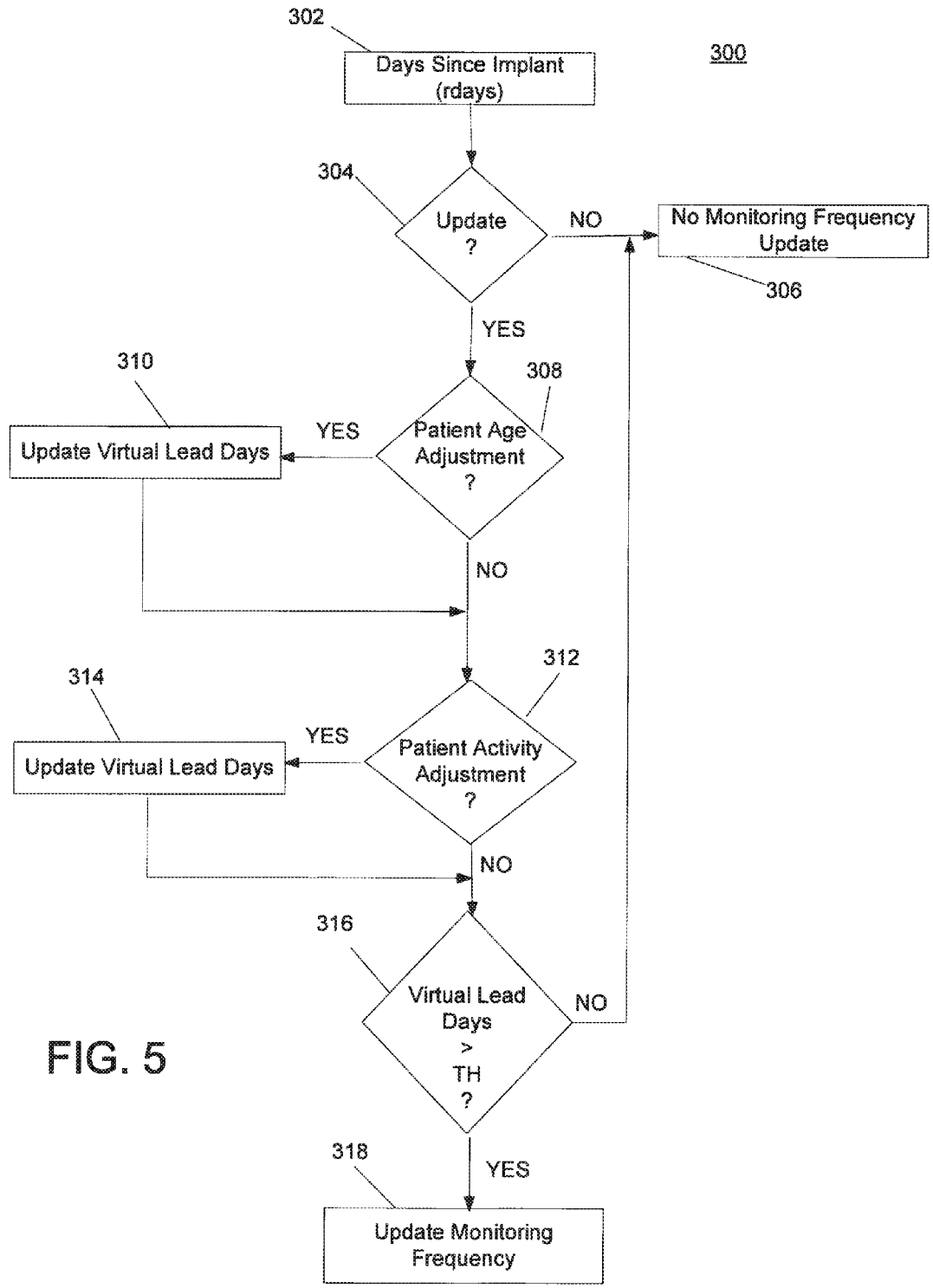
FIG. 5 is a flowchart of an exemplary method of determining lead integrity monitoring frequency in a medical device according to an embodiment of the disclosure.

FIG. 5 is a flowchart of an exemplary method of determining lead integrity monitoring frequency in a medical device according to an embodiment of the disclosure. As described above, many factors exist that may contribute to lead failure. According to an embodiment of the present disclosure, multiple patient characteristics may be utilized in order to perform the determination of lead integrity monitoring frequency. For example, as illustrated in FIG. 5, according to one embodiment, similar to the embodiment described above, the device monitors lead integrity using lead impedance measurements taken four times per day, and initially makes the determination as to whether to update the lead integrity monitoring frequency 300 by determining whether the predetermined period of time, i.e., 24 hours, has expired since implant of the device, Block 304.

If the update time period has not expired, NO in Block 304, no monitoring frequency update is performed, Block 306. Once the initial update time has expired, YES in Block 304, the device determines the current age of the patient, compares the patient's current age to a predetermined patient age adjustment threshold, and determines whether to adjust the frequency at which the lead integrity monitoring is performed based on the determined age of the patient, Block 308.

For example, in order to determine whether a patient age adjustment is to occur, Block 308, the device determines whether the age of the patient is within a predetermined patient age range, such as whether the age of the patient is greater than 20 years but less than 40 years. If the patient is determined to be within the predetermined patient age range, less than 20 years, for example, YES in Block 308, a patient age adjustment is determined to be needed. As described above, according to one embodiment, the device stores a value associated with the virtual lead days since implant of the device, which is initially equal to the running actual or "real days" since implant of the device, Block 302. If the patient age adjustment is determined to be needed, YES in Block 308, the device updates the number of virtual lead days since implant of the lead, Block 310, by increasing the number of virtual lead days by a predetermined number of days associated with a patient age adjustment. According to one embodiment, the device updates the stored virtual lead days, Block 310, by increasing the virtual lead days by a predetermined amount when the patient is determined to be within the patient adjustment range, Block 308. In one embodiment the device increases the virtual lead days, Block 310, by adding four days to the currently stored virtual lead days, for example. In this way, for each day the patient is determined to be in the predetermined patient age range, YES in Block 308, the stored virtual lead days is updated in Block 310 by being increased by four days. If the patient is determined to not be in the predetermined patient age range, NO in Block 308, no patient age adjustment to the virtual days is made.

Once the virtual lead days has been updated based on the patient's age in Block 310, or if the current patient age is not within the patient range, and therefore a patient age adjustment is not determined to be needed, NO in Block 308, the device determines the daily level of activity of the patient via electrical activity sensed via activity sensor 109 (FIG. 2), compares the patient's daily activity level to a predetermined activity level adjustment threshold, and determines whether to adjust the frequency at which the lead integrity monitoring is performed based on the determined activity level of the patient, Block 312.

For example, in order to determine whether a patient daily activity level adjustment is to occur, Block 312, the device determines whether the level of activity of the patient during the most recent time period associated with the determination in Block 304 as to whether to update the lead integrity monitoring frequency 300, i.e., 24 hours for example, is greater than the patient activity adjustment threshold. According to one embodiment, the patient activity adjustment threshold may be set at predetermined period of time, such as 400 minutes for example. If the patient activity is greater than the patient activity adjustment threshold and therefore a patient activity adjustment is determined to be needed, YES in Block 312, the device updates the number of virtual lead days since implant of the lead, Block 314, by increasing the number of virtual lead days by a predetermined number of days associated with a patient activity adjustment. In one embodiment the device increases the virtual lead days, Block 314, by adding one real lead day to the currently stored virtual lead days, for example. In this way, if the patient is determined to be engage in the predetermined level of activity, YES in Block 312, the stored accumulated virtual lead days since implant is updated in Block 314 by being increased a predetermined number of days. Therefore, the value of the virtual days includes the sum of the running real days since implant of the device and either or both the predetermined number of days associated with the patient age adjustment and the determined number of days associated with the patient activity, if applicable.

Once either the patient activity is determined to be not greater than the patient activity adjustment threshold, and therefore a patient activity adjustment is not determined to be needed, NO in Block 312, or the virtual lead days have been updated in Block 314, the device compares the updated virtual lead days to a virtual lead days threshold to determine whether the value of updated virtual lead days is greater than the virtual lead days threshold, Block 316. If the updated virtual lead days is not greater than the virtual lead days threshold, NO in Block 316, no monitoring frequency update is performed, Block 306, and the process is repeated once the next predetermined period of time, i.e., 24 hours has expired, YES in Block 304. If the current value of the updated virtual lead days is determined to be greater than the virtual lead days threshold, YES in Block 316, a monitoring frequency update is performed so that the frequency of the lead integrity monitoring is updated by a predetermined adjustment value, Block 318, and the process is repeated once the next predetermined period of time, i.e., 24 hours has expired, YES in Block 304.

As described above, according to one embodiment of the disclosure, the virtual lead days threshold may be set as five years so that the frequency of the lead integrity monitoring is increased in Block 318 once the stored updated virtual lead days is determined to be greater than five years, Block 316. The frequency of the lead integrity monitoring may be updated by increasing the number of daily impedance measurements used to evaluate lead integrity. In one embodiment, the device increases the number of daily impedance values utilized to determine lead integrity issues from the initial four impedance values per day to eight values per day.

As described above, according to another embodiment illustrated in FIG. 4, in order to update the frequency of lead integrity monitoring, Block 318, as a result of the accumulation of patient age and patient activity, the device increases the number of daily impedance values utilized to determine lead integrity issues, indicated on the upper portion of timeline 220, from the initial four impedance values determined per day 222 to eight impedance values determined per day 224 once the accumulated virtual days, indicated on the lower portion of timeline 220, are greater than 5 years 226. The device then subsequently increases the number of daily impedance values utilized to determine lead integrity issues to twelve impedance values determined per day 228 once the accumulated virtual days are greater than ten years 230, to twenty-four impedance values determined per day 232 once the accumulated virtual days are greater than fifteen years 234, to thirty-six impedance values determined per day 236 once the accumulated virtual days are greater than twenty years 238, and to forty-eight impedance values determined per day 240 once the accumulated virtual days are greater than twenty-five years 242, and so forth.

Figure 6:
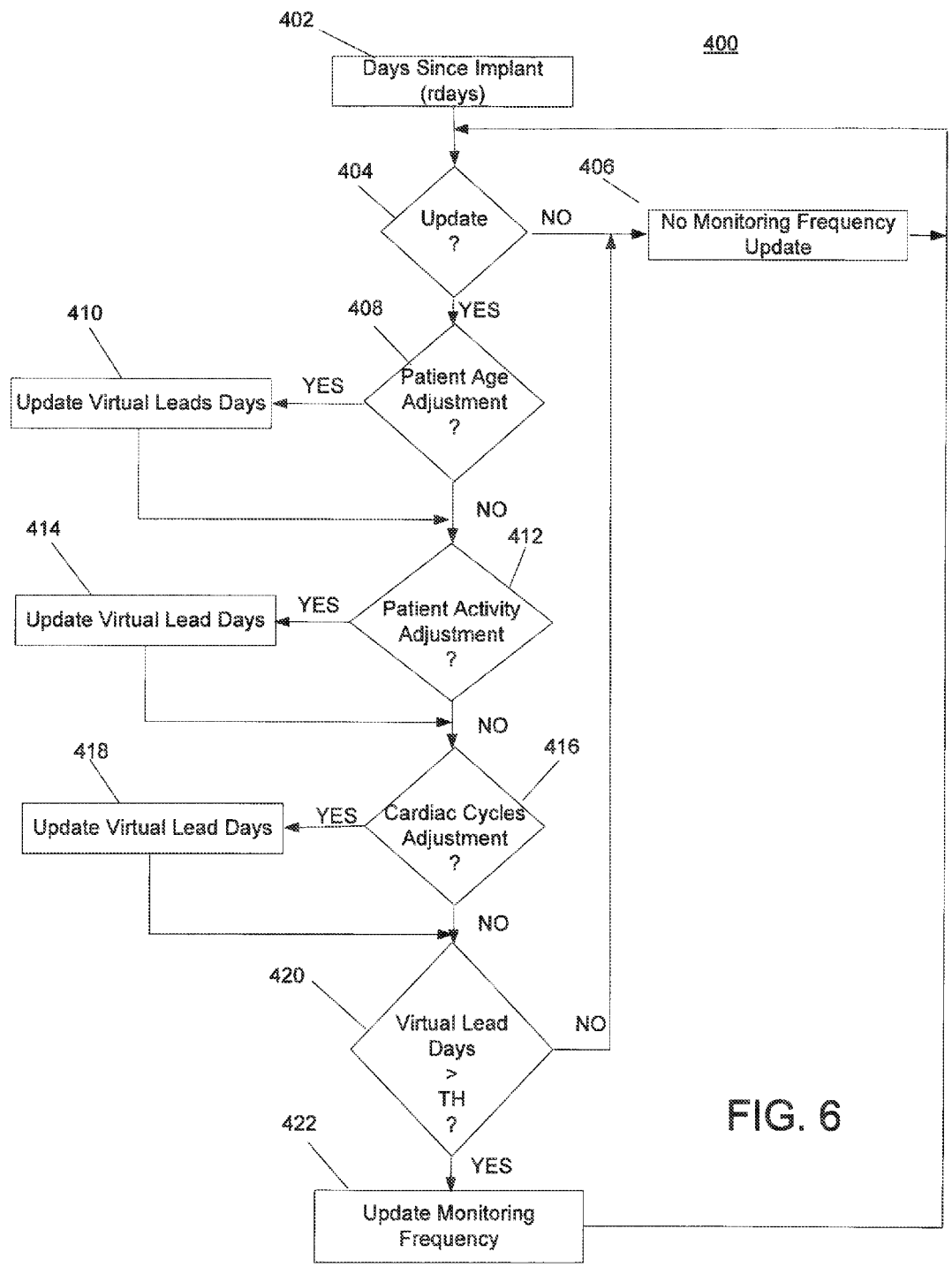
FIG. 6 is a flowchart of an exemplary method of determining lead integrity monitoring frequency in a medical device according to an embodiment of the disclosure.

FIG. 6 is a flowchart of an exemplary method of determining lead integrity monitoring frequency in a medical device according to an embodiment of the disclosure. As illustrated in FIG. 6, according to one embodiment, similar to the embodiments described above, the device monitors lead integrity using lead impedance measurements taken four times per day, and initially makes the determination as to whether to update the lead integrity monitoring frequency 400 by determining whether the predetermined period of time, i.e., 24 hours, has expired since implant of the device, Block 404.

If the update time period has not expired, NO in Block 404, no monitoring frequency update is performed, Block 406. Once the initial update time has expired, YES in Block 404, the device determines the current age of the patient, compares the patient's current age to a predetermined patient age adjustment threshold, and determines whether to adjust the frequency at which the lead integrity monitoring is performed based on the determined age of the patient, Block 408.

For example, in order to determine whether a patient age adjustment is to occur, Block 408, the device determines whether the age of the patient is within a predetermined patient age range, such as whether the age of the patient is greater than 20 years but less than 40 years. If the patient is determined to be within the predetermined patient age range, i.e., less than twenty years for example, YES in Block 408, a patient age adjustment is determined to be needed. As described above, according to one embodiment, the device stores a value associated with the virtual lead days since implant of the device, which is initially equal to the running actual or "real days" since implant of the device, Block 402. If the patient age adjustment is determined to be needed, YES in Block 408, the device updates the number of virtual lead days since implant of the lead, Block 410, by increasing the number of virtual lead days by a predetermined number of days associated with a patient age adjustment. According to one embodiment, the device updates the stored virtual lead days, Block 410, by increasing the virtual lead days by a predetermined amount when the patient is determined to be within the patient adjustment range, Block 408. In one embodiment the device increases the virtual lead days, Block 410, by adding four times the number of real lead days, Block 402, to the currently stored virtual lead days, for example. In this way, if the patient is determined to be in the predetermined patient age range, YES in Block 408, the virtual lead days since implant is updated in Block 410 by being increased by four times the number of real lead days, Block 402, since implant of the device. If the patient is determined to not be in the predetermined patient age range, NO in Block 408, no patient age adjustment to the virtual days is made.

Once the virtual lead days has been updated based on the patient's age in Block 410, or if the current patient age is not within the patient range and therefore a patient age adjustment is not determined to be needed, NO in Block 408, the device determines the daily level of activity of the patient via electrical activity sensed via activity sensor 109 (FIG. 2), compares the patient's daily activity level to a predetermined activity level adjustment threshold, and determines whether to adjust the frequency at which the lead integrity monitoring is performed based on the determined activity level of the patient, Block 412.

For example, in order to determine whether a patient daily activity level adjustment is to occur, Block 412, the device determines whether the level of activity of the patient during the most recent time period associated with the determination in Block 404 as to whether update the lead integrity monitoring frequency 400, i.e., 24 hours for example, is greater than the patient activity adjustment threshold. According to one embodiment, the patient activity adjustment threshold may be set at predetermined period of time, such as 400 minutes for example. According to another embodiment, the activity sensor may generate a signal corresponding to the number of steps the patient takes per day, and therefore the patient activity adjustment threshold may be set as 8,000 steps per day. If the patient activity is greater than the patient activity adjustment threshold and therefore a patient activity adjustment is determined to be needed, YES in Block 412, the device updates the number of virtual lead days since implant of the lead, Block 414, by increasing the number of virtual lead days by a predetermined number of days associated with a patient activity adjustment. For example, in one embodiment the device increases the virtual lead days, Block 414, by adding one real lead day to the currently stored virtual lead days, for example. In this way, if the patient is determined to be engage in the predetermined level of activity, YES in Block 412, the stored virtual lead days since implant is updated in Block 414 by being increased a predetermined number of days.

Another factor that may contribute to the possible occurrence of lead failure is the amount of flexing of the lead that occurs. As the number of times the lead is flexed increases, the possibility of lead failure may increase. Therefore, according to one embodiment, in addition to being updated in response to patient age and activity, the device may also utilize the patient heart rate, as a metric of the number of lead flexes that occur over the lifetime of the lead, as an indicator of whether to update the frequency of lead integrity monitoring. For example, the device may determine the number of cardiac cycles via activity sensor 109 (FIG. 2), compares the number of cardiac cycles to a predetermined cardiac cycle adjustment threshold, and determines whether to adjust the frequency at which the lead integrity monitoring is performed based on the determined number of cardiac cycles that occur during a given time period, Block 416.

For example, in order to determine whether a number of cardiac cycle adjustment is to occur, Block 416, the device determines whether the number of cardiac cycles of the patient during the most recent time period associated with the determination in Block 404 as to whether to update the lead integrity monitoring frequency 400, i.e., 24 hours for example, is greater than the cardiac cycle adjustment threshold. According to one embodiment, the cardiac cycle adjustment threshold is set at predetermined number of cardiac cycles, such as 10,000 cycles, for example. If the number of cardiac cycles is greater than the cardiac cycle adjustment threshold and therefore a patient cardiac cycle adjustment is determined to be needed, YES in Block 416, the device updates the number of virtual lead days since implant of the lead, Block 418, by increasing the number of virtual lead days by a predetermined number of days associated with a patient cardiac cycle adjustment. In one embodiment the device increases the virtual lead days, Block 418, by adding one real lead day to the currently stored virtual lead days, for example. Therefore, the value of the virtual days includes the sum of the running real days since implant of the device and either one or a combination of the predetermined number of days associated with the patient age adjustment, the determined number of days associated with the patient activity adjustment and the determined number of days associated with patient cardiac cycle adjustment, if applicable.

Once at least one of the patient age, patient activity, and number of cardiac cycles and determined and the virtual lead days updated accordingly, Blocks 408-418, the device compares the updated virtual lead days to a virtual lead days threshold to determine whether the value of updated virtual lead days is greater than the virtual lead days threshold, Block 420. If the updated virtual lead days is not greater than the virtual lead days threshold, NO in Block 420, no monitoring frequency update is performed, Block 406, and the process is repeated once the next predetermined period of time, i.e., 24 hours has expired, YES in Block 404. If the current value of the updated virtual lead days is determined to be greater than the virtual lead days threshold, YES in Block 420, a monitoring frequency update is performed so that the frequency of the lead integrity monitoring is updated by a predetermined adjustment value, Block 422, and the process is repeated once the next predetermined period of time, i.e., 24 hours has expired, YES in Block 404.

As described above, according to one embodiment of the disclosure, the virtual lead days threshold may be set as five years so that the frequency of the lead integrity monitoring is increased in Block 422 once the stored updated virtual lead days is determined to be greater than five years, Block 420. The frequency of the lead integrity monitoring may be updated by increasing the number of daily impedance measurements used to evaluate lead integrity. In one embodiment, the device increases the number of daily impedance values utilized to determine lead integrity issues from the initial four impedance values per day to eight values per day.

As described above, according to another embodiment illustrated in FIG. 4, in order to update the frequency of lead integrity monitoring, Block 422, as a result of the accumulation of patient age and patient activity, the device increases the number of daily impedance values utilized to determine lead integrity issues, indicated on the upper portion of timeline 220, from the initial four impedance values determined per day 222 to eight impedance values determined per day 224 once the accumulated virtual days, indicated on the lower portion of timeline 220, are greater than 5 years 226. The device then subsequently increases the number of daily impedance values utilized to determine lead integrity issues to twelve impedance values determined per day 228 once the accumulated virtual days are greater than ten years 230, to twenty-four impedance values determined per day 232 once the accumulated virtual days are greater than fifteen years 234, to thirty-six impedance values determined per day 236 once the accumulated virtual days are greater than twenty years 238, and to forty-eight impedance values determined per day 240 once the accumulated virtual days are greater than twenty-five years 242, and so forth.

Figure 7:
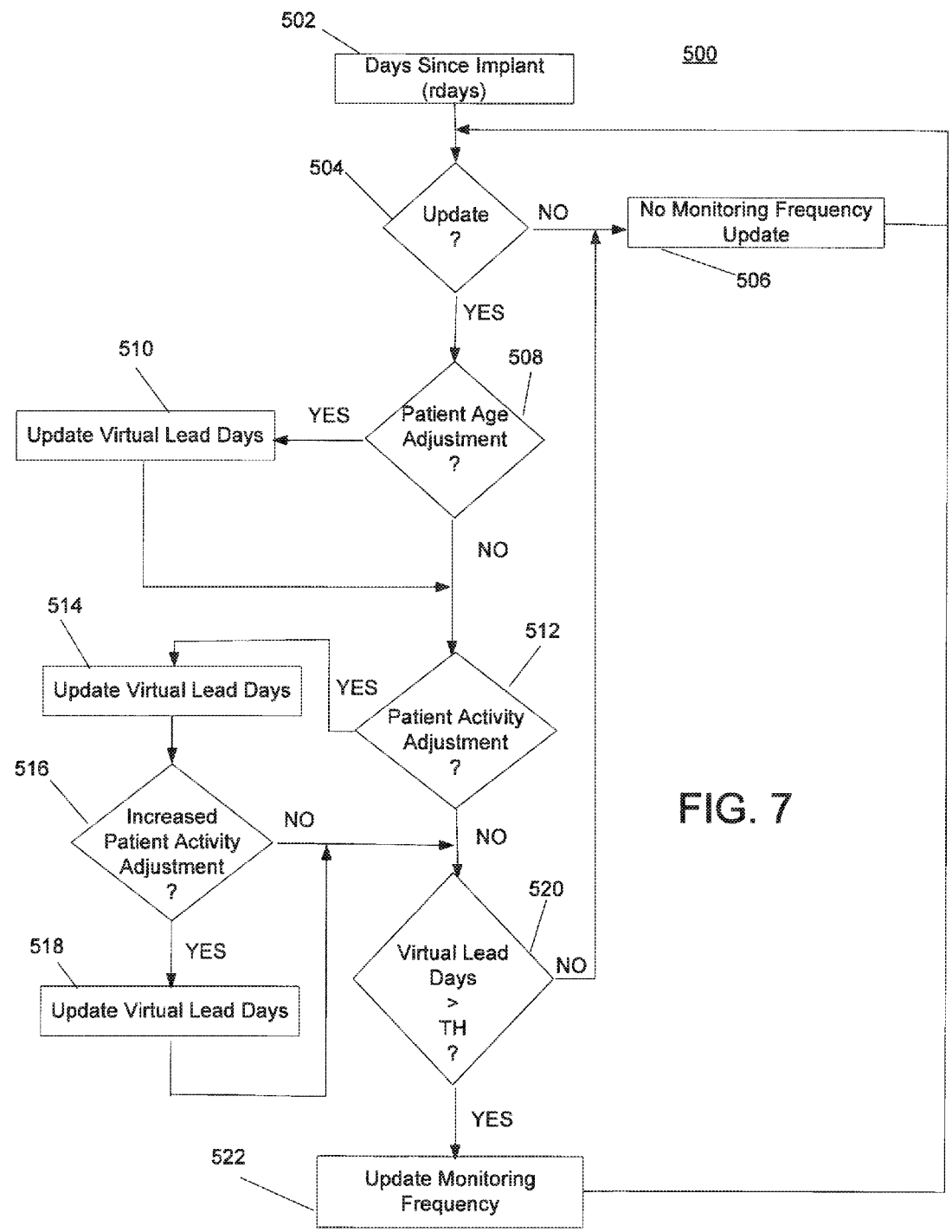
FIG. 7 is a flowchart of an exemplary method of determining lead integrity monitoring frequency in a medical device according to an embodiment of the disclosure.

FIG. 7 is a flowchart of an exemplary method of determining lead integrity monitoring frequency in a medical device according to an embodiment of the disclosure. As illustrated in FIG. 7, according to another embodiment, the device monitors lead integrity using lead impedance measurements taken four times per day, and initially makes the determination as to whether to update the lead integrity monitoring frequency 500 by determining whether the predetermined period of time, i.e., 24 hours, has expired since implant of the device, Block 504.

If the update time period has not expired, NO in Block 504, no monitoring frequency update is performed, Block 506. Once the initial update time has expired, YES in Block 504, the device determines the current age of the patient, compares the patient's current age to a predetermined patient age adjustment threshold, and determines whether to adjust the frequency at which the lead integrity monitoring is performed based on the determined age of the patient, Block 508.

For example, in order to determine whether a patient age adjustment is to occur, Block 508, the device determines whether the age of the patient is within a predetermined patient age range, such as whether the age of the patient is less than 20 years, for example. If the patient is determined to be within the predetermined patient age range, YES in Block 508, a patient age adjustment is determined to be needed. As described above, according to one embodiment, the device stores a value associated with the virtual lead days since implant of the device, which is initially equal to the running actual or "real days" since implant of the device, Block 502. If the patient age adjustment is determined to be needed, YES in Block 508, the device updates the number of virtual lead days since implant of the lead, Block 510, by increasing the number of virtual lead days by a predetermined number of days associated with a patient age adjustment. According to one embodiment, the device updates the stored virtual lead days, Block 510, by increasing the virtual lead days by a predetermined amount when the patient is determined to be within the patient adjustment range, Block 508. In one embodiment the device increases the virtual lead days, Block 510, by adding four times the number of real lead days, Block 502, to the currently stored virtual lead days, for example. In this way, if the patient is determined to be in the predetermined patient age range, YES in Block 508, the virtual lead days since implant is updated in Block 510 by being increased by four times the number of real lead days, Block 502, since implant of the device. If the patient is determined to not be in the predetermined patient age range, NO in Block 508, no patient age adjustment to the virtual days is made. Therefore, the value of the virtual days includes the sum of the running real days since implant of the device and the predetermined number of days associated with the patient age adjustment, if applicable.

Once the virtual lead days has been updated based on the patient's age in Block 510, or if the current patient age is not within the patient range, and therefore a patient age adjustment is not determined to be needed, NO in Block 508, the device determines the daily level of activity of the patient via electrical activity sensed via activity sensor 109 (FIG. 2), compares the patient's daily activity level to a predetermined activity level adjustment threshold, and determines whether to adjust the frequency at which the lead integrity monitoring is performed based on the determined activity level of the patient, Block 512. For example, in order to determine whether a patient daily activity level adjustment is to occur, Block 512, the device determines whether the level of activity of the patient during the most recent time period associated with the determination in Block 504 as to whether to update the lead integrity monitoring frequency 300, i.e., 24 hours for example, is greater than the patient activity adjustment threshold. According to one embodiment, the patient activity adjustment threshold may be set at predetermined period of time, such as 400 minutes for example. If the patient activity is greater than the patient activity adjustment threshold and therefore a patient activity adjustment is determined to be needed, YES in Block 512, the device updates the number of virtual lead days since implant of the lead, Block 514, by increasing the number of virtual lead days by a predetermined number of days associated with a patient activity adjustment. In one embodiment the device increases the virtual lead days, Block 514, by adding one real lead day to the currently stored virtual lead days, for example. In this way, if the patient is determined to be engaged in the predetermined level of activity, YES in Block 512, the stored accumulated virtual lead days since implant is updated in Block 514 by being increased a predetermined number of days.

As described above, two factors that may contribute to the occurrence of issues leading to failure of the lead are the age and the level of activity of the patient, with an increase in the number of lead integrity issues occurring for younger patients and patients who are more active. Since both factors may contribute to increased risk of integrity issues occurring, there may be reason to include a weighting of how these factors are considered in determining integrity monitoring frequency. For example, a patient who is within the increased risk age group and is relatively active may need to be distinguished from a person within the increased risk age group who is extremely active. In addition, a person outside the increased risk age group may be so active that the risk of lead integrity issues for that person may be similar to the person who is within the increased risk age group but who is only relatively active. Therefore, according to one embodiment, once the device determines that the patient is within the patient age range, YES in Block 508, that a patient activity level adjustment is necessary, YES in Block 512, and updates the value of the virtual lead days accordingly, Blocks 510 and 514, the device may determine whether an increased patient activity level adjustment to the stored virtual lead days should be made, Block 516.

In particular, in order to distinguish extremely active and relatively active patients who have both been identified as being within the increased risk age group, the device compares the patient's daily activity level to a second predetermined activity level adjustment threshold, Block 516, that is greater than the first activity level adjustment threshold previously utilized in Block 512. According to one embodiment, the first activity level adjustment threshold associated with the first patient activity adjustment determination, Block 512, is set at 400 minutes, as described above, and the second patient activity level adjustment threshold associated with the second patient activity adjustment determination, Block 516, is set at 450 minutes, for example.

If the patient activity level is greater than the second patient activity adjustment threshold, YES in Block 516, and therefore an increased patient activity adjustment is determined to be needed, the device updates the number of virtual lead days since implant of the lead, Block 518, a second time by further increasing the number of virtual lead days by a predetermined number of days associated with an extreme patient activity adjustment. In one embodiment the device additionally increases the virtual lead days, Block 518, by adding one real lead day to the currently stored virtual lead days, for example. In this way, if the patient is determined to be engage in the predetermined extreme level of activity, YES in Block 516, the stored accumulated virtual lead days since implant is further updated by being increased an additional predetermined number of days.

According to another embodiment, in order to identify a patient who is outside the increased risk age group who nevertheless may be so active that the risk of lead integrity issues for that patient may be similar to the patient who is within the increased risk age group, if the device determines that the current patient age is not within the patient range, and therefore a patient age adjustment is not determined to be needed, NO in Block 508, but a patient activity adjustment is determined to be needed, YES in Block 512, and therefore the device updates the number of virtual lead days since implant of the lead, Block 514, by increasing the number of virtual lead days by a predetermined number of days associated with a patient activity adjustment, the devices then compares the patient's daily activity level to a second predetermined activity level adjustment threshold, Block 516, that is greater than the first activity level adjustment threshold previously utilized in Block 512. According to this embodiment, the first activity level adjustment threshold associated with the first patient activity adjustment determination, Block 512, is set at 400 minutes, as described above, and the second patient activity level adjustment threshold associated with the second patient activity adjustment determination, Block 516, is set being weighted based on the amount that the activity level is greater than the first activity level adjustment threshold previously utilized in Block 512. For example, according to one embodiment, the stored virtual days are increased a predetermined number of days for each predetermined number of minutes that the activity level is greater than the first activity level adjustment threshold previously utilized in Block 512, i.e. greater than 400 minutes. In one embodiment the stored virtual days may be increased one day for each 50 minutes of activity greater than the first activity level adjustment threshold previously utilized in Block 512. Therefore, the stored virtual days are increased an additional day once the activity level reaches 450 minutes, for example, or four additional days if the activity level reaches 600 minutes.

Once either the patient activity is determined to be not greater than the patient activity adjustment threshold, and therefore a patient activity adjustment is not determined to be needed, NO in Block 512, or the virtual lead days have been updated in Block 514 or in both Block 514 and Block 518, the device compares the resulting updated virtual lead days to a virtual lead days threshold to determine whether the value of updated virtual lead days is greater than the virtual lead days threshold, Block 520. If the updated virtual lead days is not greater than the virtual lead days threshold, NO in Block 520, no monitoring frequency update is performed, Block 506, and the process is repeated once the next predetermined period of time, i.e., 24 hours has expired, YES in Block 504. If the current value of the updated virtual lead days is determined to be greater than the virtual lead days threshold, YES in Block 520, a monitoring frequency update is performed so that the frequency of the lead integrity monitoring is updated by a predetermined adjustment value, Block 522, and the process is repeated once the next predetermined period of time, i.e., 24 hours has expired, YES in Block 504.

As described above, according to one embodiment of the disclosure, the virtual lead days threshold may be set as five years so that the frequency of the lead integrity monitoring is increased in Block 522 once the stored updated virtual lead days is determined to be greater than five years, YES in Block 520. The frequency of the lead integrity monitoring may be updated by increasing the number of daily impedance measurements used to evaluate lead integrity. In one embodiment, the device increases the number of daily impedance values utilized to determine lead integrity issues from the initial four impedance values per day to eight values per day.

As described above, according to another embodiment illustrated in FIG. 4, in order to update the frequency of lead integrity monitoring, Block 522, the device increases the number of daily impedance values utilized to determine lead integrity issues, indicated on the upper portion of timeline 220, from the initial four impedance values determined per day 222 to eight impedance values determined per day 224 once the accumulated virtual days, indicated on the lower portion of timeline 220, are greater than 5 years 226. The device then subsequently increases the number of daily impedance values utilized to determine lead integrity issues to twelve impedance values determined per day 228 once the accumulated virtual days are greater than ten years 230, to twenty-four impedance values determined per day 232 once the accumulated virtual days are greater than fifteen years 234, to thirty-six impedance values determined per day 236 once the accumulated virtual days are greater than twenty years 238, and to forty-eight impedance values determined per day 240 once the accumulated virtual days are greater than twenty-five years 242, and so forth.

Figure 8:
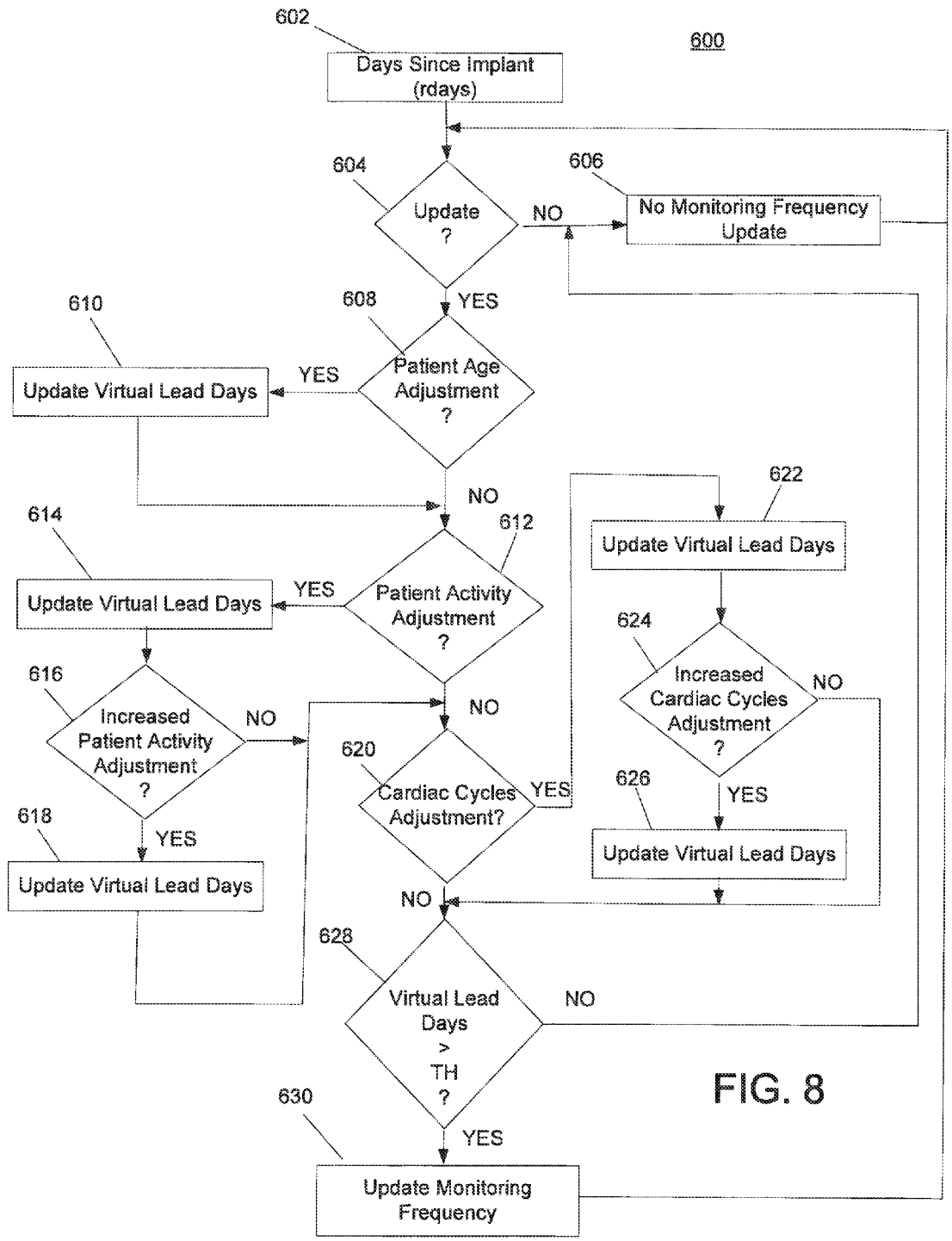
FIG. 8 is a flowchart of an exemplary method of determining lead integrity monitoring frequency in a medical device according to an embodiment of the disclosure.

FIG. 8 is a flowchart of an exemplary method of determining lead integrity monitoring frequency in a medical device according to an embodiment of the disclosure. According to one embodiment, the number of cardiac cycles may be utilized in place of patient activity or in combination with patient activity, as shown in FIG. 8. For the sake of brevity, the determination of whether the patient is within the patient age range and/or is determined to have a predetermined level activity, Blocks 602-618 of FIG. 8 have been described above in reference to FIG. 7 and will not be repeated.

As illustrated in FIG. 8, As illustrated in FIG. 8, the device may also determine the number of cardiac cycles via activity sensor 109 (FIG. 2), compare the number of cardiac cycles to a predetermined cardiac cycle adjustment threshold, and determine whether to adjust the frequency at which the lead integrity monitoring is performed based on the determined number of cardiac cycles that occur during a given time period, Block 620.

For example, in order to determine whether a number of cardiac cycle adjustment is to occur, Block 620, the device determines whether the number of cardiac cycles of the patient during the most recent time period associated with the determination in Block 604 as to whether to update the lead integrity monitoring frequency 400, i.e., 24 hours for example, is greater than the cardiac cycles adjustment threshold. According to one embodiment, the cardiac cycles adjustment threshold may be set at predetermined number of cardiac cycles, such as 100,000 cycles, for example. If the number of cardiac cycles is greater than the cardiac cycles adjustment threshold and therefore a patient cardiac cycles adjustment is determined to be needed, YES in Block 620, the device updates the number of virtual lead days since implant of the lead, Block 622, by increasing the number of virtual lead days by a predetermined number of days associated with a patient cardiac cycles adjustment. In one embodiment the device increases the virtual lead days, Block 622, by adding one real lead day to the currently stored virtual lead days, for example.

According to the embodiment of FIG. 8, in order to distinguish extremely active and relatively active patients who have both been identified as being within the increased risk age group, the device compares the patient's determined number of cardiac cycles to a second cardiac cycles adjustment threshold, Block 624, that is greater than the first cardiac cycles adjustment threshold previously utilized in Block 620. According to one embodiment, the first cardiac cycles adjustment threshold associated with the first patient cardiac cycles adjustment determination, Block 620, is set at 100,000 cardiac cycles, as described above, and the second patient cardiac cycles adjustment threshold associated with the second patient cardiac cycles adjustment determination, Block 624, is set at 110,000 cardiac cycles, for example.

If the number of cardiac cycles is greater than the second cardiac cycles adjustment threshold, YES in Block 624, and therefore an increased patient activity adjustment is determined to be needed, the device updates the number of virtual lead days since implant of the lead, Block 626, a second time by further increasing the number of virtual lead days by a predetermined number of days associated with an extreme patient cardiac cycles adjustment. In one embodiment the device additionally increases the virtual lead days, Block 626, by adding one half of real lead day to the currently stored virtual lead days, for example.

According to another embodiment, the second patient cardiac cycles adjustment threshold associated with the second patient cardiac cycles adjustment determination, Block 624, may be set being weighted based on the amount that the number of cardiac cycles are greater than the first cardiac cycles adjustment threshold previously utilized in Block 620. For example, according to one embodiment, the stored virtual days are increased a predetermined number of days for each predetermined number of minutes that the number of cardiac cycles are greater than the first cardiac cycles adjustment threshold previously utilized in Block 620, i.e. greater than 100,000 cycles. In one embodiment the stored virtual days may be increased one half of a day for each 10,000 cycles that the number of cardiac cycles are greater than the first cardiac cycles adjustment threshold previously utilized in Block 620. Therefore, the stored virtual days are increased an additional half-day once the number of cardiac cycles reaches 110,000 cycles, for example, or two additional days if the number of cardiac cycles reaches 140,000 cardiac cycles.

Figure 9:
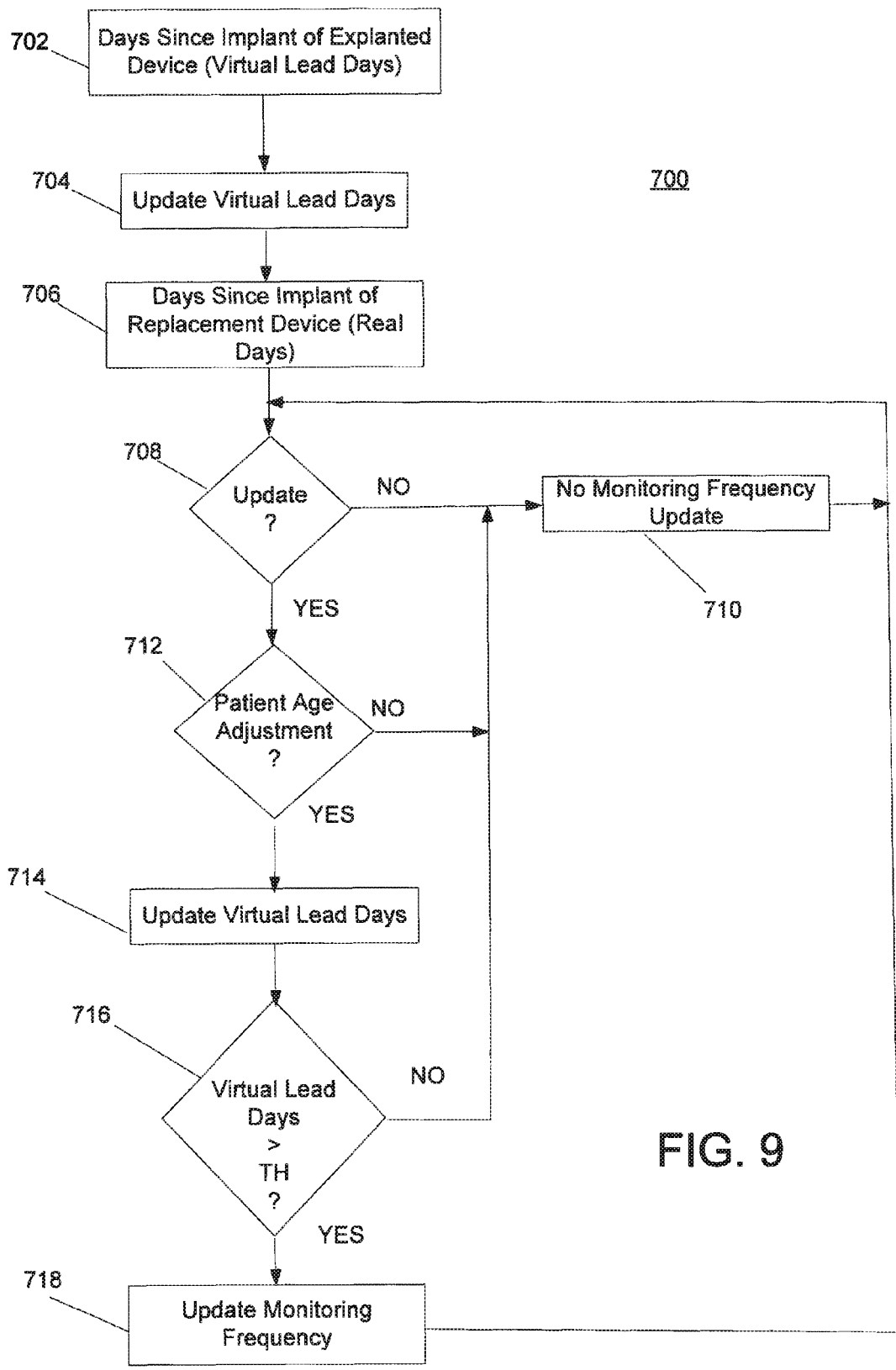
FIG. 9 is a flowchart of an exemplary method of determining lead integrity monitoring frequency in a medical device according to an embodiment of the disclosure.

FIG. 9 is a flowchart of an exemplary method of determining lead integrity monitoring frequency in a medical device according to an embodiment of the disclosure. In certain instances, such as when a battery becomes depleted, it may become necessary for the device to be removed from the patient and replaced by a replacement device. Typically, as long as the lead of the device is still in a satisfactory operable condition, this "device change out" involves disconnecting the lead from the header of the housing, or can of the device, and removing and replacing only the removed housing. If the device being removed and replaced included and utilized the method and apparatus for determining lead integrity monitoring frequency described above, the value of the updated virtual lead days may simply be transferred from the device being removed to the new device being implanted, and the determination of whether to update the lead integrity monitoring frequency described above would continue. However, if the apparatus for determining lead integrity monitoring frequency described above was not included or utilized in the device being removed and replaced by a new device, it may be necessary to initialize the virtual days in the replacement device to be updated to account for the time period that the lead was utilized while connected to the device being explanted.

Therefore, as illustrated in FIG. 9, during implant of the replacement device within the patient and connection of the replacement device housing to the prior implanted lead, information such as one or more of the age of the patient, the gender of the patient, the date of implant of the device currently being explanted, the date of implant of the implanted lead, and the date of implant of the replacement device may be stored in the replacement device by being input by the implanting physician using a programmer. In addition, the initial frequency at which lead integrity monitoring, such as impedance monitoring, for example, is performed may also be set by the physician via the programmer, or a default starting frequency may be utilized. The number of days since the implant of the explanted device and the number of days since implant of the lead, Block 702, is either determined by the physician at the time of the implant of the replacement device and input in the replacement device by the physician, or may be determined by the replacement device using the stored date of the explanted device. Of course, unless more than one explant procedure has occurred, the number of days since implant of the explanted device, i.e., the housing or can, is the same as the number of days since implant of the lead, since both were implanted at the same time.

The replacement device updates the virtual lead days, Block 704, which is initially set equal to the running actual or "real days" since implant of the replacement device, by increasing the value of the stored virtual lead days by the number of days since the implant of the explanted device. For example, if the explanted device was removed four years after being implanted and replaced by the replacement device, the replacement device would set the initial value of the stored virtual lead days to four years.

If the current device explant and replacement procedure is not the first explant procedure associated with the lead at issue, meaning that the explanted housing or can is not the same housing or can that was initially implanted simultaneously with the lead, additional information such as the date that the lead was implanted may also be determined, if such information is available.

As illustrated in FIG. 9, once the initial value of the virtual lead days is updated in Block 704 to reflect the life of the lead while connected to the explanted device, or if the current explant change out procedure is not the first explant procedure to take place, to reflect the actual period of time the lead has been implanted, updating of the frequency of lead integrity monitoring may be determined in ways similar to any of the embodiments described above. For example, according to one embodiment, lead integrity issues may be monitored using impedance measurements taken four times per day, and the device performs the determination 700 of whether to update the lead integrity monitoring frequency once per day, i.e. once every 24 hours. However, the frequency of the lead impedance monitoring and/or the frequency at which the determination of whether to update the lead integrity monitoring frequency 700 may also initially be performed at other desired frequencies, such as twice a day or once every two days, for example.

Therefore, as illustrated in FIG. 9, according to an embodiment of the present disclosure, the replacement device monitors lead integrity using lead impedance measurements taken four times per day, and initially makes the determination as to whether to update the lead integrity monitoring frequency 700 by determining whether the predetermined period of time, i.e., 24 hours, has expired since implant of the device, Block 708. If the update time period has not expired, NO in Block 708, no monitoring frequency update is performed, Block 710. Once the initial update time has expired, YES in Block 708, the replacement device determines the current age of the patient, compares the patient's current age to a predetermined patient age adjustment threshold, and determines whether to update the frequency at which the lead integrity monitoring is performed based on the determined age of the patient, Block 712.

For example, in order to determine whether a patient age adjustment is to occur, Block 712, the replacement device determines whether the age of the patient is within a predetermined patient age range, such as whether the age of the patient is less than 20 years. If the current patient age is not within the patient range, NO in Block 714, no update of the frequency of performance of the lead integrity monitoring is made, Block 710, the replacement device continues performing the lead integrity monitoring at the current monitoring frequency, and waits until the next frequency update monitoring is scheduled to occur, Block 708, i.e., the replacement device again waits for 24 hours, and the process is repeated.

If the patient is determined to be within the predetermined patient age range, YES in Block 712, a patient age adjustment is determined to be needed. If the patient age adjustment is determined to be needed, YES in Block 712, the replacement device initially updates the previously determined updated virtual lead days by increasing the value of the number of virtual lead days by a predetermined number of days associated with a patient age adjustment, Block 714.

The replacement device may update the stored virtual lead days, Block 714, by increasing the virtual lead days by a predetermined amount when the patient is determined to be within the patient adjustment range, Block 712. In one embodiment the replacement device increases the virtual lead days, Block 714, by adding four days to the currently stored virtual lead days, for example. In this way, for each day the patient is determined to be in the predetermined patient age range, YES in Block 712, the stored virtual lead days is updated in Block 714 by being increased by four days.

Once the virtual lead days have been updated in Block 714, the replacement device compares the updated virtual lead days to a virtual lead days threshold to determine whether the value of updated virtual lead days is greater than the virtual lead days threshold, Block 716. If the updated virtual lead days is not greater than the virtual lead days threshold, NO in Block 716, no monitoring frequency update is performed, Block 710, and the process is repeated once the next predetermined period of time, i.e., 24 hours has expired, YES in Block 708. If the current updated virtual lead days are determined to be greater than the virtual lead days threshold, YES in Block 716, the frequency of the lead integrity monitoring is updated by a patient age adjustment value, Block 718, and the process is repeated once the next predetermined period of time, i.e., 24 hours has expired, YES in Block 708.

As described above, according to one embodiment of the disclosure, the virtual lead days threshold may be set as five years so that the frequency of the lead integrity monitoring is increased in Block 718 once the stored updated virtual lead days is determined to be greater than five years, Block 716. The frequency of the lead integrity monitoring may be updated by increasing the number of daily impedance measurements used to evaluate lead integrity. In one embodiment, the replacement device increases the number of daily impedance values utilized to determine lead integrity issues from the initial four impedance values per day to eight values per day.

As described above, according to another embodiment illustrated in FIG. 4, in order to update the frequency of lead integrity monitoring, Block 718, as a result of the accumulation of the updated lead virtual days resulting from both the update to account for the time period that the lead was utilized while connected to the replacement device being explanted, Block 704 and the determined patient age, Block 714, the replacement device increases the number of daily impedance values utilized to determine lead integrity issues, indicated on the upper portion of timeline 220, from the initial four impedance values determined per day 222 to eight impedance values determined per day 224 once the accumulated virtual days, indicated on the lower portion of timeline 220, are greater than 5 years 226. The replacement device then subsequently increases the number of daily impedance values utilized to determine lead integrity issues to twelve impedance values determined per day 228 once the accumulated virtual days are greater than ten years 230, to twenty-four impedance values determined per day 232 once the accumulated virtual days are greater than fifteen years 234, to thirty-six impedance values determined per day 236 once the accumulated virtual days are greater than twenty years 238, and to forty-eight impedance values determined per day 240 once the accumulated virtual days are greater than twenty-five years 242, and so forth.

Figure 10:
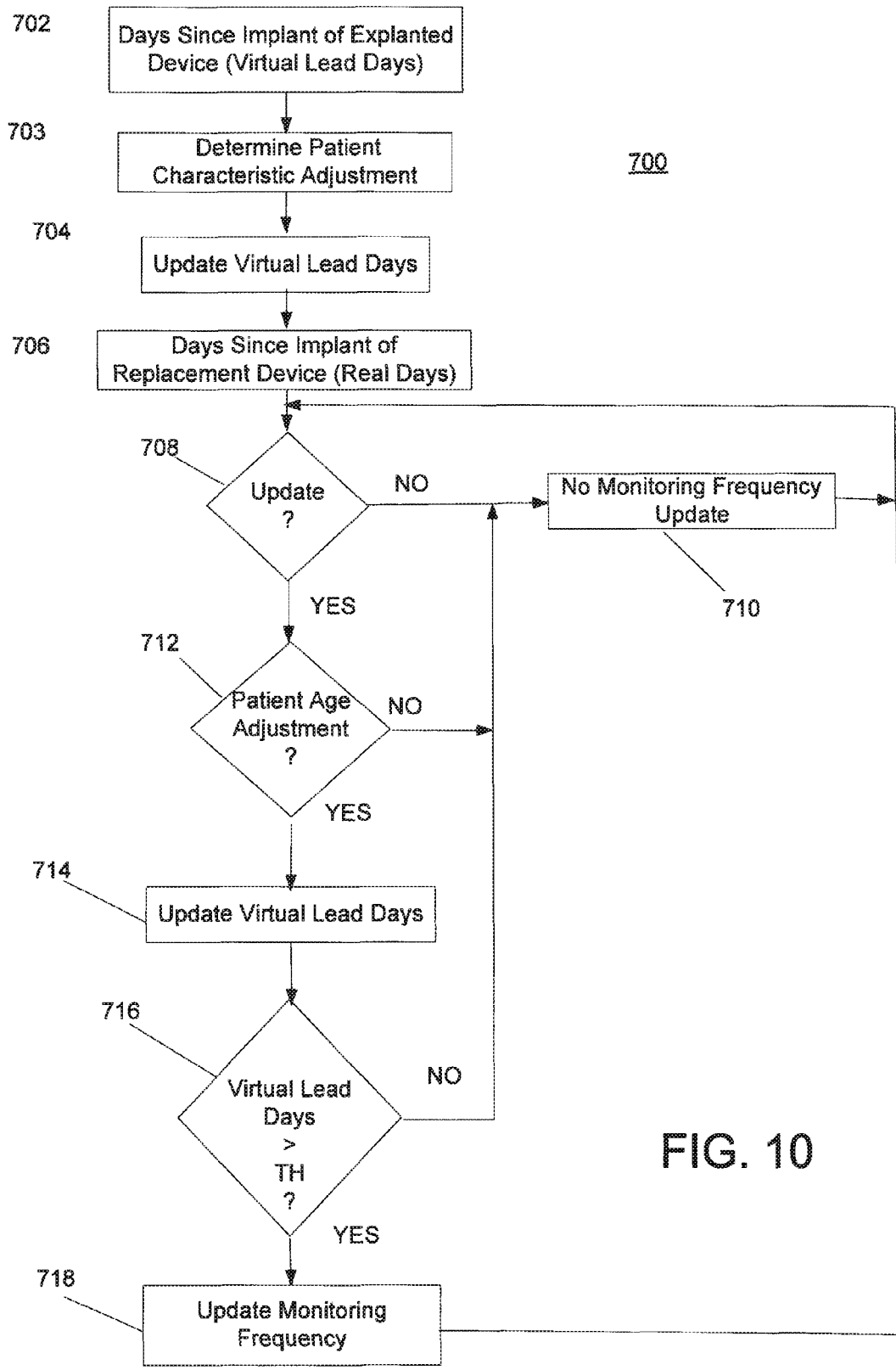
FIG. 10 is a flowchart of an exemplary method of determining lead integrity monitoring frequency in a medical device according to an embodiment of the disclosure.

FIG. 10 is a flowchart of an exemplary method of determining lead integrity monitoring frequency in a medical device according to an embodiment of the disclosure. During replacement of the device, factors other than merely the number of days since implant of the lead may be utilized to update the virtual lead days stored in the replacement device. Therefore, according to an embodiment, updating of the virtual lead days stored in the replacement device may include the number of days since implant of the lead in combination with an additional patient characteristic, such as daily activity or number of the cardiac cycles during a predetermined period of time, as described above.

For example, as illustrated in FIG. 10, according to one embodiment, during implant of the replacement device within the patient and connection of the replacement device to the prior implanted lead, information such as one or more of the age of the patient, the gender of the patient, the date of implant of the explanted device, and the date of implant of the replacement device may be stored in the device by being input by the implanting physician using a programmer. In addition, the initial frequency at which lead integrity monitoring, such as impedance monitoring, for example, may also be set by the physician via the programmer, or a default starting frequency may be utilized. The number of days since the implant of the explanted device, and therefore the number of days since the implant of the lead (assuming a first explant procedure), Block 702, is either determined by the physician at the time of the implant of the replacement device and input in the replacement device by the physician, or may be determined by the replacement device using the stored date of the explanted device. In addition, the replacement device may determine one or more patient characteristics using data stored in the explanted device, Block 703, to be utilized in determining the value of the updated virtual lead days stored in the replacement device.

According to one embodiment, using the age of the patient at implant of the explanted device, the replacement device determines the number of days that the patient's age was less than a predetermined threshold prior to the explanted device being removed, Block 703. For example, according to one embodiment, the replacement device uses information stored in the explanted device (or input by the physician) to determine the number of days that the patient's age was less than a patient age threshold prior to the explant procedure, and updates the initial value of the stored virtual lead days by a predetermined number of days for each day that the patient's age was less than the patient age threshold. In one embodiment, the replacement device determines the number of days that the patient's age was less than twenty years old, and updates the value of the stored virtual lead days by four days for each day that the patient's age was less than the patient age threshold. According to another embodiment, the replacement device determines the number of days that the patient's age was within a range, such as between twenty and forty years, for example, and updates the value of the stored virtual lead days by four days for each day that the patient's age was within the patient age range.

The replacement device updates the virtual lead days, Block 704, which is initially set equal to the running actual or "real days" since implant of the lead, by increasing the current value of the stored virtual lead days by the sum of the number of days since the implant of the lead, Block 702, and the determined patient characteristic adjustment, Block 703. For example, if the explanted device was removed four years after being implanted and replaced by the replacement device, and the patient was 22 years old at the time of replacement, the number of days since the implant of the explanted device, Block 702, would be four years (assuming first explant), and the number of days that the patient's age was within the patient age range (less than 20 years), Block 703, would be 2 years. According to one embodiment, for each update period that the patient is determined to have been in the predetermined patient age range, the stored virtual lead days is updated in Block 210 by being increased by four days. Therefore, the patient characteristic adjustment to the virtual lead days, Block 703, would result in an adjustment of 8 years (2 years×4=8 years). The replacement device therefore would set the initial value of the stored virtual lead days, Block 704, to twelve years (4 years (real days since initial lead implant)+8 years (patient characteristic adjustment)).

In the same way, according to another embodiment, the determination of the patient character adjustment in Block 703 may include a determination of the activity level of the patient occurring prior to the explanted device being removed. For example, assuming a first explant procedure and using data stored in the explanted device, the replacement device may compare data stored in the explanted device relating to the patient's daily activity level to a predetermined activity level adjustment threshold, and update the value of the stored virtual lead days in Block 704 accordingly. According to one embodiment, the replacement device determines the number of days that the patient daily activity level is greater than a predetermined threshold, such as 400 minutes for example.

During the updating of the stored virtual lead days in Block 704, if the explanted device was removed four years after being implanted and replaced by the replacement device, the patient was 22 years old at the time of replacement, and the patient had a daily activity level greater than the activity level threshold on 100 days, the patient characteristic adjustment in Block 703 would result in an adjustment of 8 years (2 years× 4=8 years) and 100 days. According to one embodiment, the replacement device updates the virtual lead days, Block 704, by increasing the value of the stored virtual lead days by the sum of the number of days since the implant of the explanted device, Block 702, and the determined patient characteristic adjustment, Block 703. Therefore, the replacement device would set the initial value of the stored virtual lead days, Block 704, to twelve years (4 years (days since initial lead/device implant)+(8 years and 100 days) (patient characteristic adjustment)).

These and other patient characteristics having values stored in the explanted device may also be utilized, alone or in combination, such as the number of cardiac cycles that occur during a given time period prior to the explanted device being removed. For example, the determination of the patient characteristic adjustment, Block 703, may include determining the number of cardiac cycles that occur during a given time period, so the replacement device determines the number of times the daily number of cardiac cycles of the patient was greater than a cardiac cycle adjustment threshold, such as 100,000 cycles, for example. The replacement device updates the lead virtual days, Block 704, by increasing the virtual lead days by one day for each day the number of daily cardiac cycles exceed the cardiac cycle adjustment threshold in addition to the determined number of days since implant of the lead, Block 702, and any other patient characteristics that may be desired in the patient characteristic adjustment in Block 703.

Once the value of the stored virtual lead days has been update in Block 704, the replacement device determines whether to update the lead integrity monitoring frequency, Blocks 708-718 as described above, and therefore the description associated with Blocks 708-715 will not be repeated for brevity sake. It is also understood that updating of the stored virtual lead days in the replacement device may include any combination or single use of the days that the explanted device was implanted and or any one or more patient character adjustments available in the explanted device. In addition, it is also understood that, while the updating of the stored virtual lead days in the replacement device is shown only in combination with the use of patient activity (similar to FIG. 3) to determine whether to update the lead integrity monitoring frequency, Blocks 708-718, the updating of the stored virtual lead days in the replacement device may be utilized in combination with other embodiments for determining whether to update the lead integrity monitoring frequency, such as any of the embodiments described above.

Thus, a medical device and associated methods for monitoring lead integrity have been presented in the foregoing description with reference to specific embodiments. Various combinations or modifications of the illustrative embodiments may be conceived by one having ordinary skill in the art based on the teachings provided herein. For example, other resolutions for updating of the frequency of lead integrity monitoring may be utilized in addition to those described above in reference to FIG. 4. For example, according to another embodiment, the integrity monitoring frequency may be increased by two for each incremental year of virtual lead years. As a result, the integrity monitoring frequency would be increased from four times per day to six times per day once the virtual lead days increased to a year, to eight times per day once the virtual lead days increased to two years, to ten times per day once the virtual lead days reached three years, and so forth. Thus it is appreciated that various modifications to the referenced embodiments may be made without departing from the scope of the disclosure as set forth in the following claims.

I claim:

1. A medical device, comprising:
   a device housing containing electronic circuitry;
   a lead electrically coupled to the housing;
   an electrode positioned along the lead to sense a cardiac signal and to deliver cardiac therapy; and
   a processor positioned within the housing and configured to determine whether a lead condition is occurring in response to the sensed cardiac signal, determine whether a first patient characteristic is satisfied during a plurality of predetermined update periods, perform a first update of a virtual lead days value associated with a number of days since implant of the lead in response to the first patient characteristic being satisfied, determine whether a patient characteristic update is satisfied in response to a second patient characteristic, different than the first patient characteristic, being satisfied, perform a second update of the virtual lead days value in response to the patient characteristic update being satisfied, and update a frequency of determining whether the lead condition is occurring in response to the updated virtual lead days value.

2. The medical device of claim 1, wherein the first patient characteristic comprises a patient age and the processor is configured to perform the first update of the virtual lead days value in response to the patient age being within a predetermined patient age range and to not perform the first update of the virtual lead days value in response to the patient age being outside the predetermined patient age range.

3. The medical device of claim 2, wherein the second patient characteristic comprises a patient activity level and processor is configured to determine the patient characteristic update is satisfied in response to the patient activity level being greater than a predetermined patient activity level threshold.

4. The medical device of claim 1, wherein the processor is configured to compare the updated virtual lead days to a plurality of predetermined thresholds, and increase the frequency of determining whether the lead condition is occurring in response to the comparing.

5. The medical device of claim 1, wherein the second patent characteristic comprises a number of cardiac cycles and the processor is configured to determine the patient characteristic update is satisfied in response to the number of cardiac cycles being greater than a predetermined cardiac cycles threshold.

6. The medical device of claim 5, wherein the first patient characteristic comprises a patient age and the processor is configured to perform the first update of the virtual lead days value in response to the patient age being within a predetermined patient age range and to not perform the first update of the virtual lead days value in response to the patient age being outside the predetermined patient age range.

7. The medical device of claim 1, wherein the processor is configured to compare the updated virtual lead days to a plurality of predetermined thresholds, and increase the frequency of determining whether the lead condition id occurring in response to the comparing.

8. The medical device of claim 1, wherein second patient characteristic comprises a patient activity level and a number of cardiac cycles, and the processor is configured to determine the patient characteristic update is satisfied in response to one or both the patient activity level being greater than a predetermined patient activity level threshold and the number of cardiac cycles being greater than a predetermined cardiac cycles threshold.

9. The medical device of claim 8, wherein the first patient characteristic comprises a patient age and the processor is configured to perform the first update of the virtual lead days value in response to the patient age being within a predetermined patient age range and to not perform the first update of the virtual lead days value in response to the patient age being outside the predetermined patient age range.

10. The medical device of claim 1, wherein the processor is configured to compare the updated virtual lead days to a plurality of predetermined thresholds, and increase the frequency of determining whether the lead condition is occurring in response to the comparing.

11. The medical device of claim 1, wherein the processor is configured to determine one or more impedance values in response to the delivered therapy a predetermined number of times during a predetermined time period, determine whether the lead condition is occurring in response to the determined one or more impedance values, and update the frequency of determining whether the lead condition is occurring in response to the increased predetermined number of times.

12. A method for updating a frequency of determining whether a lead condition is occurring in a medical device, comprising:
sensing a cardiac signal;
determining whether a lead condition is occurring in response to the sensed cardiac signal;
determining whether a first patient characteristic is satisfied during a plurality of predetermined update periods;
performing a first update of a virtual lead days value associated with a number of days since implant of the lead in response to the first patient characteristic being satisfied;
determining whether a patient characteristic update is satisfied in response to a second patient characteristic, different than the first patient characteristic, being satisfied;
performing a second update of the virtual lead days value in response to the patient characteristic update being satisfied; and
updating a frequency of determining whether the lead condition is occurring in response to the updated virtual lead days value.

13. The method of claim 12, wherein the first patient characteristic comprises a patient age and further comprising:
performing the first update of the virtual lead days value in response to the patient age being within a predetermined patient age range; and
not perform the first update of the virtual lead days value in response to the patient age being outside the predetermined patient age range.

14. The method of claim 13, wherein the second patient characteristic comprises a patient activity level and further comprising determining the patient characteristic update is satisfied in response to the patient activity level being greater than a predetermined patient activity level threshold.

15. The method of claim 12, further comprising:
comparing the updated virtual lead days to a plurality of predetermined thresholds; and
increasing the frequency of determining whether the lead condition is occurring in response to the comparing.

16. The method of claim 12, wherein the second patent characteristic comprises a number of cardiac cycles and further comprising determining the patient characteristic update is satisfied in response to the number of cardiac cycles being greater than a predetermined cardiac cycles threshold.

17. The method of claim 16, wherein the first patient characteristic comprises a patient age and further comprising:
performing the first update of the virtual lead days value in response to the patient age being within a predetermined patient age range; and
not performing the first update of the virtual lead days value in response to the patient age being outside the predetermined patient age range.

18. The method of claim 12, further comprising:
comparing the updated virtual lead days to a plurality of predetermined thresholds; and
increasing the frequency of determining whether the lead condition id occurring in response to the comparing.

19. The method of claim 12, wherein the first patient characteristic comprises a patient age and further comprising:
performing the first update of the virtual lead days value in response to the patient age being within a predetermined patient age range; and
not performing the first update of the virtual lead days value in response to the patient age being outside the predetermined patient age range.

20. The method of claim 19, wherein second patient characteristic comprises a patient activity level and a number of cardiac cycles, and further comprising determining the patient characteristic update is satisfied in response to one or both the patient activity level being greater than a predetermined patient activity level threshold and the number of cardiac cycles being greater than a predetermined cardiac cycles threshold.

21. The method of claim 12, wherein the processor is configured to compare the updated virtual lead days to a plurality of predetermined thresholds, and increase the frequency of determining whether the lead condition id occurring in response to the comparing.

22. The method of claim 12, further comprising:
determining one or more impedance values in response to the delivered therapy a predetermined number of times during a predetermined time period;
determining whether the lead condition is occurring in response to the determined one or more impedance values; and
updating the frequency of determining whether the lead condition is occurring in response to the increased predetermined number of times.

23. A non-transitory computer readable medium storing a set of instructions which when implemented in a medical device cause the device to perform a method for updating a frequency of determining whether a lead condition is occurring, the method comprising:
- sensing a cardiac signal;
- determining whether a lead condition is occurring in response to the sensed cardiac signal;
- determining whether a first patient characteristic is satisfied during a plurality of predetermined update periods;
- performing a first update of a virtual lead days value associated with a number of days since implant of the lead in response to the first patient characteristic being satisfied;
- determining whether a patient characteristic update is satisfied in response to a second patient characteristic, different than the first patient characteristic, being satisfied;
- performing a second update of the virtual lead days value in response to the patient characteristic update being satisfied; and
- updating a frequency of determining whether the lead condition is occurring in response to the updated virtual lead days value.

* * * * *